United States Patent
Western et al.

[11] Patent Number: 5,882,857
[45] Date of Patent: *Mar. 16, 1999

[54] INTERNAL POSITIVE CONTROLS FOR NUCLEIC ACID AMPLIFICATION

[75] Inventors: Linda M. Western, San Mateo; Samuel J. Rose, Los Altos; Edwin F. Ullman, Atherton, all of Calif.

[73] Assignee: Behringwerke AG, Marburg, Germany

[*] Notice: The terminal 13 months of this patent has been disclaimed.

[21] Appl. No.: 475,283

[22] Filed: Jun. 7, 1995

[51] Int. Cl.[6] .............................. C12Q 1/68; C12P 19/34; C07H 21/04; C07H 21/02
[52] U.S. Cl. .................................. 435/6; 435/5; 435/91.2; 536/24.3; 536/24.32; 536/24.33; 536/23.1
[58] Field of Search .................... 435/6, 5, 91.2; 536/24.3–24.33

[56] References Cited

U.S. PATENT DOCUMENTS

| | | | |
|---|---|---|---|
| 5,091,310 | 2/1992 | Innis | 435/91 |
| 5,314,809 | 5/1994 | Erlich et al. | 435/91.2 |
| 5,334,515 | 8/1994 | Rastichian et al. | 435/91.2 |
| 5,340,728 | 8/1994 | Grosz et al. | 435/91.2 |
| 5,348,853 | 9/1994 | Wang et al. | 435/6 |
| 5,411,875 | 5/1995 | Jones | 435/91.2 |

FOREIGN PATENT DOCUMENTS

| | | |
|---|---|---|
| 0373352 | 6/1990 | European Pat. Off. . |
| 0 549 107 | 6/1993 | European Pat. Off. . |
| 0 586 112 | 3/1994 | European Pat. Off. . |
| 0 640 691 | 1/1995 | European Pat. Off. . |
| WO 94/03472 | 2/1994 | WIPO . |

OTHER PUBLICATIONS

Launer et al. "Simple method for cDNA amplification starting from small amount of total RNA" Molekuliarnia Genetika Mikrobiologia, I Virusolonga 6: 38–41, 1994.
Becker Andre et al. NAR 17: 9437–9446, 1989.
Gilliand et al. PNAS 87: 2725–2729, 1990.
Ferre, PCR Methods and Applications 2: 1–9, 1992.

*Primary Examiner*—W. Gary Jones
*Assistant Examiner*—Dianne Rees
*Attorney, Agent, or Firm*—Theodore J. Leitereg

[57] ABSTRACT

The present invention relates to an improvement in a method for amplifying a target sequence of a target polynucleotide. The method comprises combining a sample suspected of containing the target polynucleotide with reagents for amplifying the target sequence and subjecting the combination to conditions wherein the target sequence if present is amplified. The present improvement comprises including in the combination a control oligonucleotide and a control polynucleotide that has a sequence that is hybridizable with the control oligonucleotide. When the control oligonucleotide is bound to the control polynucleotide, the ability of a primer to chain extend along the control polynucleotide is reduced. Optionally, the control oligonucleotide is part of the control polynucleotide. The method finds particular application in the area of nucleic acid amplification and detection.

61 Claims, 5 Drawing Sheets

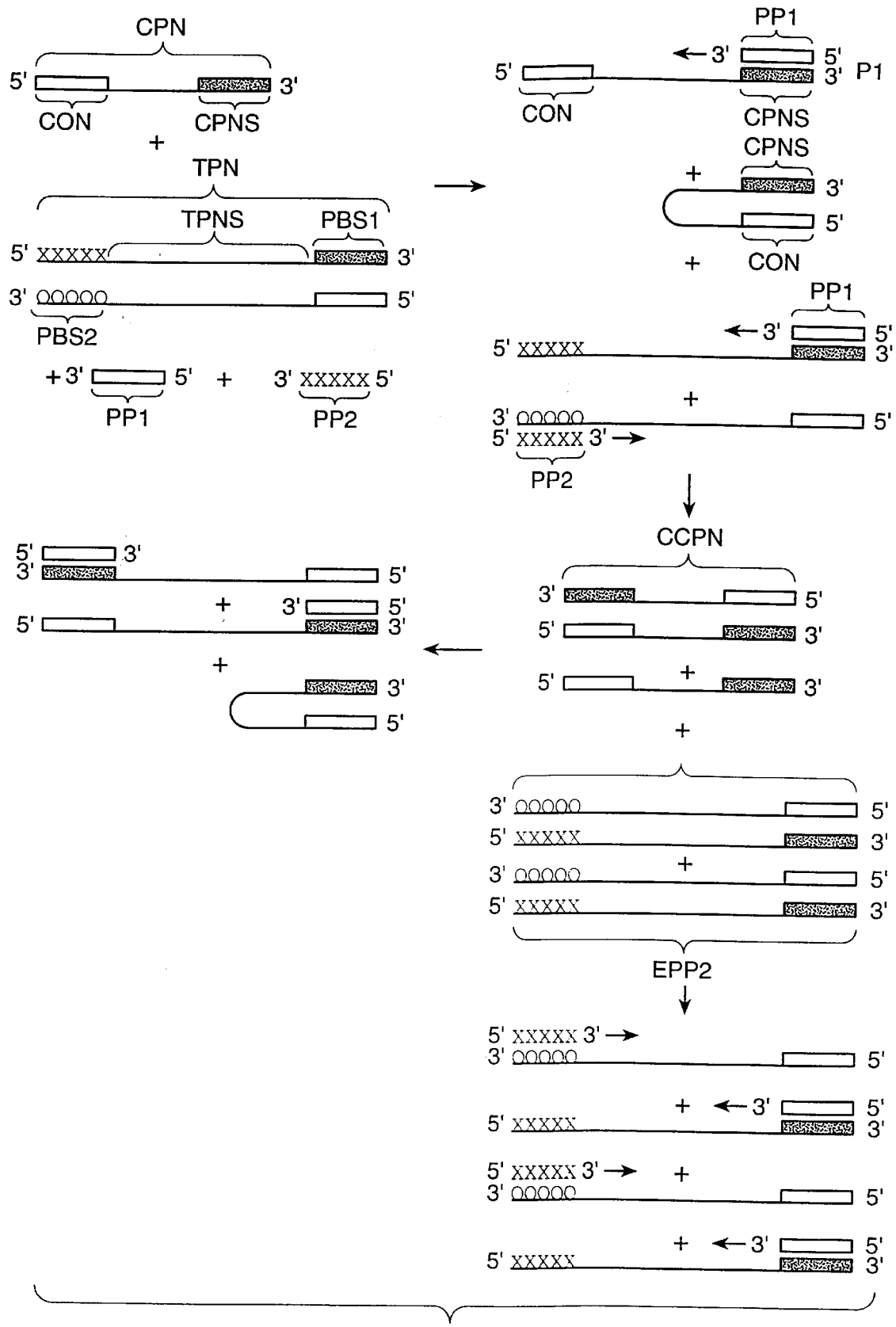
FIG._1

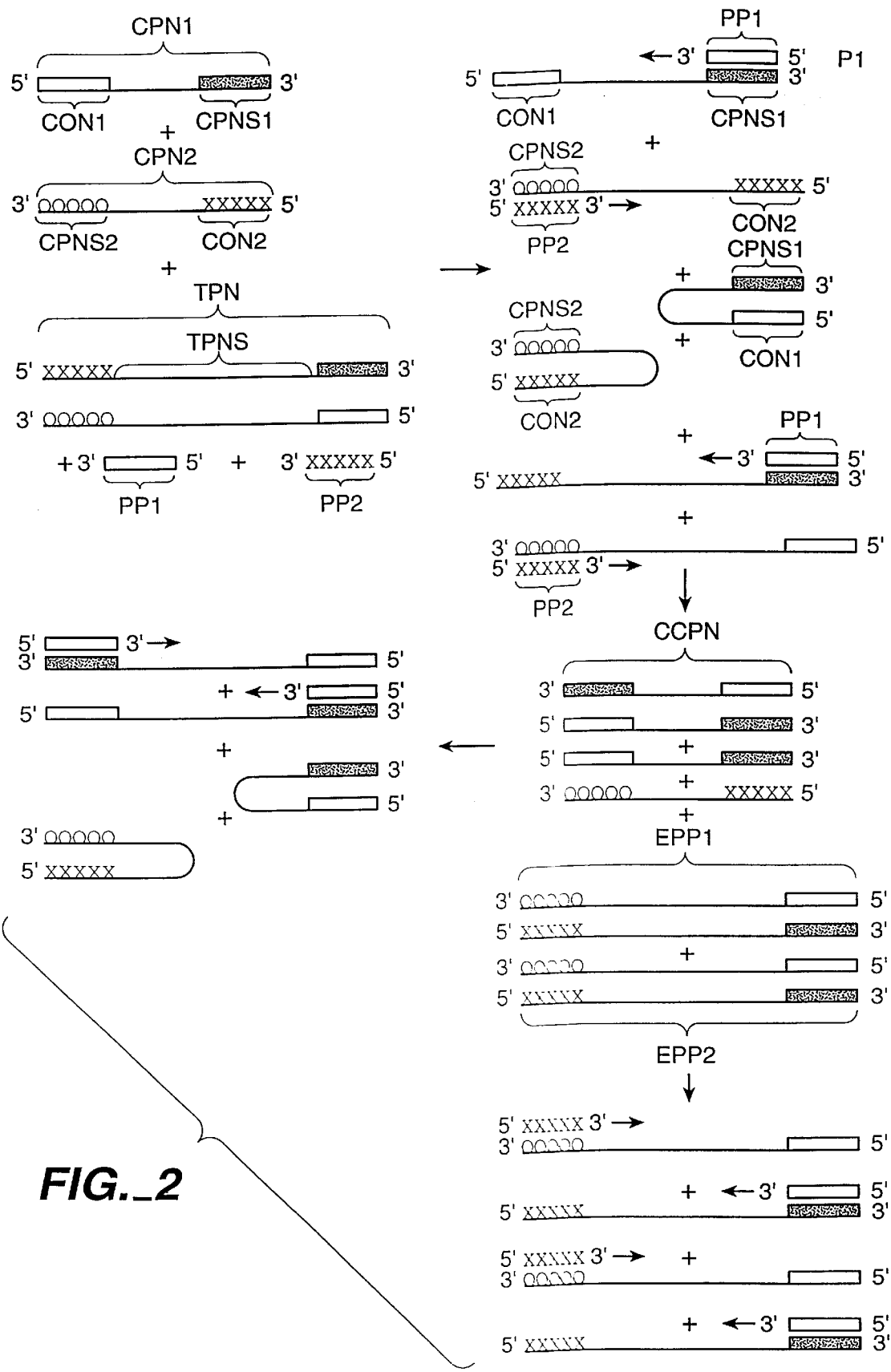
FIG._2

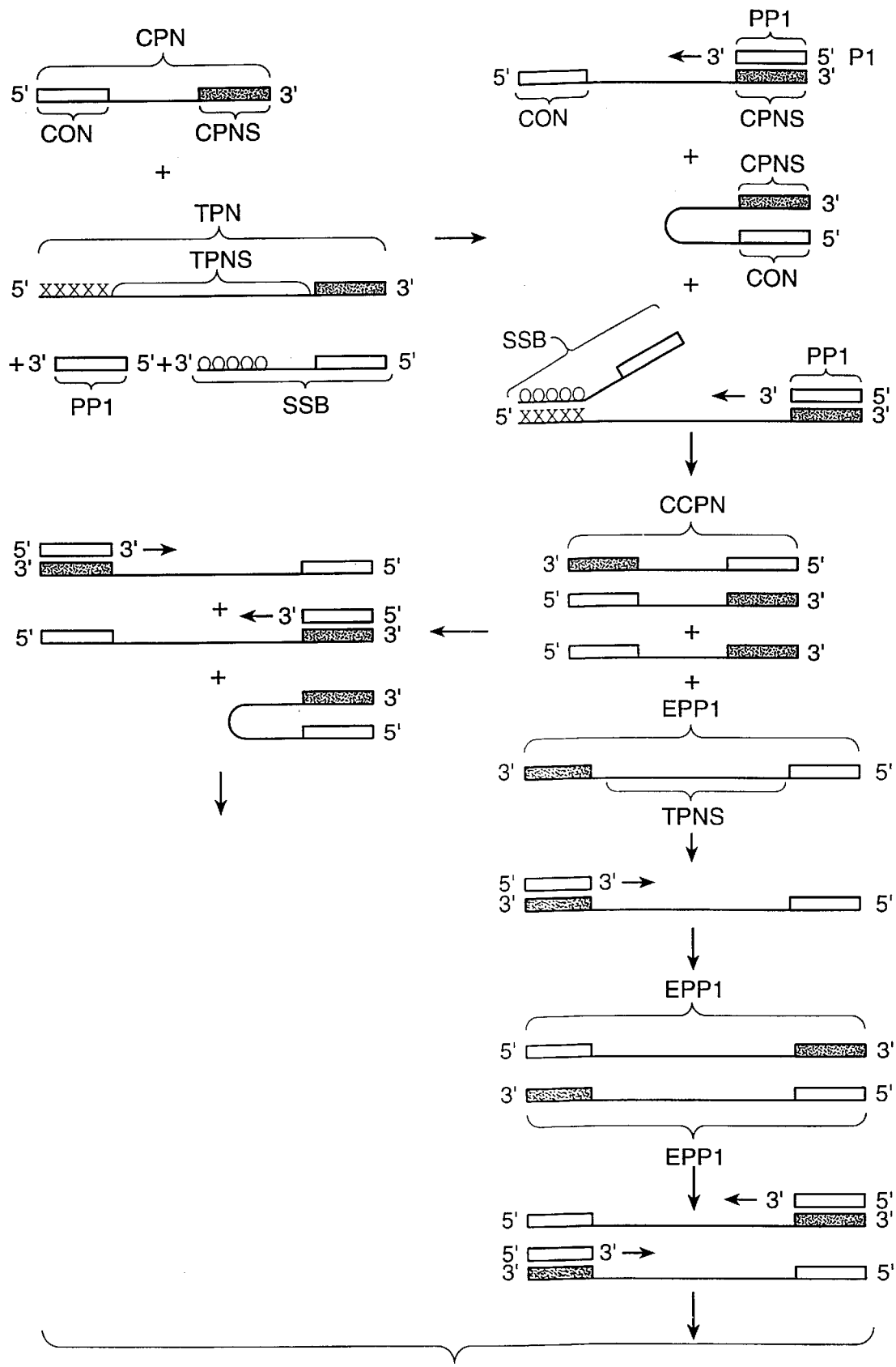
FIG._3

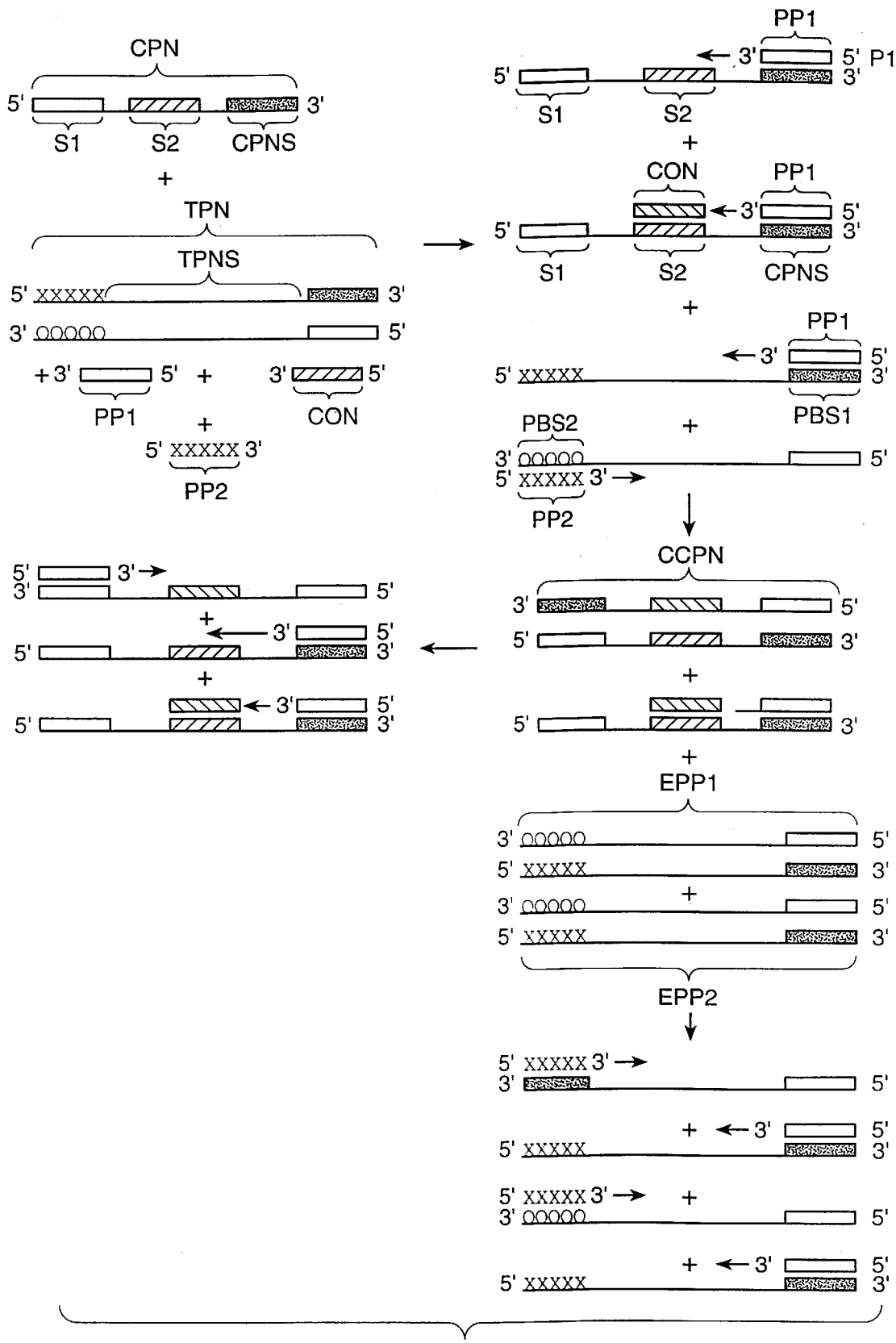
FIG._4

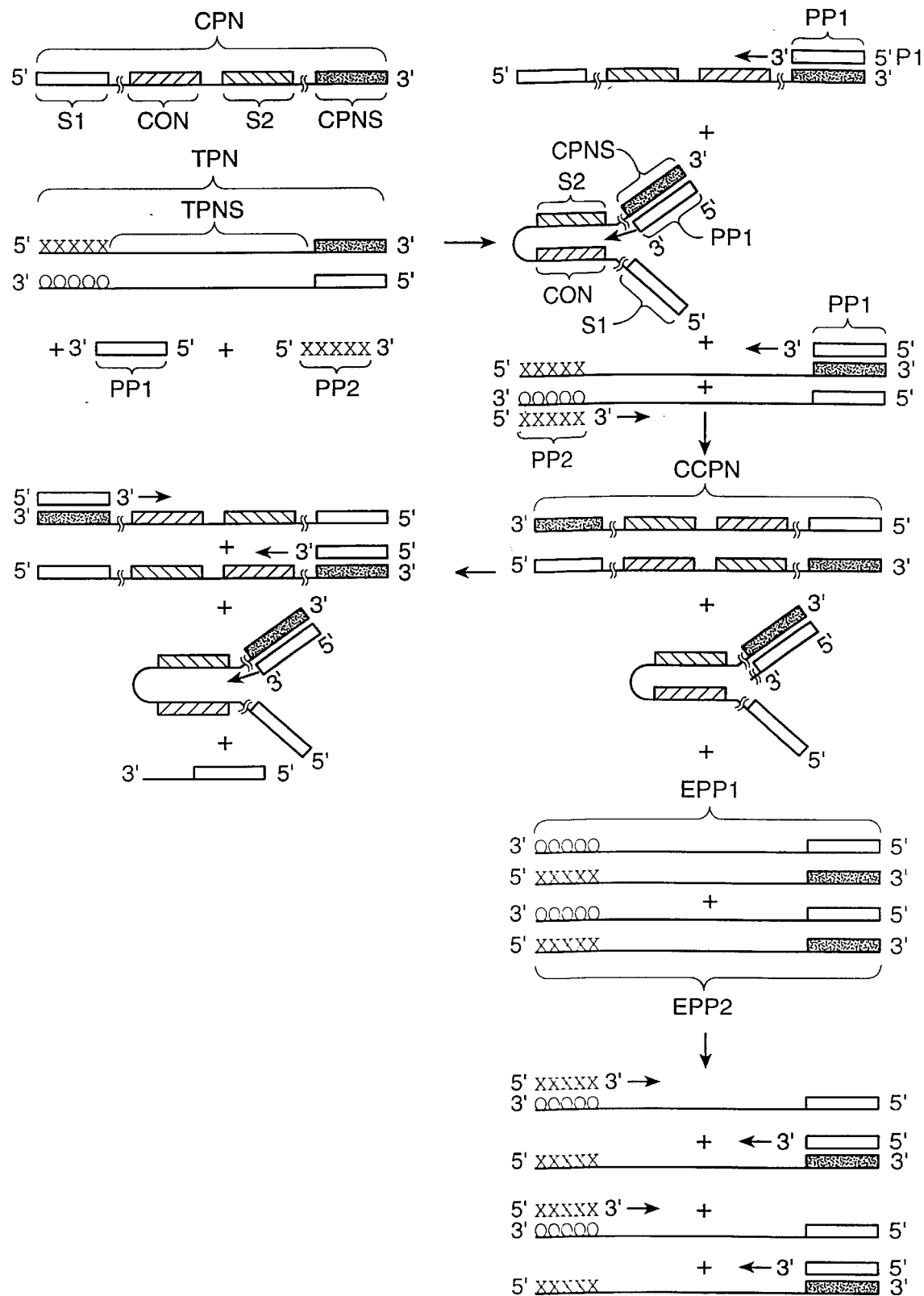
FIG._5

INTERNAL POSITIVE CONTROLS FOR NUCLEIC ACID AMPLIFICATION

BACKGROUND OF THE INVENTION

1. Field of the Invention

Significant morbidity and mortality are associated with infectious diseases. More rapid and accurate diagnostic methods are required for better monitoring and treatment of disease. Molecular methods using DNA probes, nucleic acid hybridizations and in vitro amplification techniques are promising methods offering advantages to conventional methods used for patient diagnoses.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}$p labelling of DNA with T4 polynucleotide kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

One method for detecting specific nucleic acid sequences generally involves immobilization of a target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, such a method is slow and labor intensive, and nonisotopic labels that are less readily detected than radiolabels are frequently not suitable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Another method has also recently been described for amplifying nucleic acid sequences. This method is referred to as single primer amplification. The method provides for the amplification of a target sequence that possesses a stem-loop or inverted repeat structure where the target sequence is flanked by relatively short complementary sequences. Various methods for creating such a target sequence in relation to the presence of a polynucleotide analyte to be detected have also been described.

The above methods are extremely powerful techniques for high sensitivity detection of target DNA molecules present in very small amounts. The correlation between the number of original target DNA molecules and the number of specifically amplified products is influenced by a number of variables. Minor variations in buffer or temperature conditions can greatly influence reaction-to-reaction amplification efficiencies. Further, clinical samples of DNA targets can contain inhibitory factors that can suppress enzymatic amplification.

When amplifying a target sequence of a nucleic acid for use in clinical diagnostics, there is a need to assure that each amplification reaction is capable of yielding an amplified product. In particular commercial diagnostic products require validation measures to avoid misdiagnosis due to improper assay methods or contaminated or inactive reagents. Of importance is the development of an internal positive control for demonstrating that the reagents and the detection methodology are working properly. Without such a control the failure of an assay to show the presence of a target nucleic acid sequence may be due to the absence of the target or may be caused by a failure of one or more reagents or of an instrument used in conducting an assay.

Various approaches have been developed for qualification or quantitation of amplification reactions and these approaches can be divided into two main categories, namely, homologous controls and heterologous controls. Such controls have been applied to amplification of mRNA and adapted for DNA analytes. Heterologous controls have a control polynucleotide that does not contain target sequences. One such approach is known as the "endogenous standard" assay, which utilizes as a standard an endogenous polynucleotide that is expressed at a relatively constant level in all samples to be tested. The level of the test sequence is then compared to the standard. Heterologous controls are commonly amplified regions of human DNA such as HLA-DQ and beta-globin genes or mRNA. Heterologous controls assure the adequacy of all the non-target specific reagents and the procedure but are insensitive to any problem involving a target-specific reagent.

Homologous controls utilize a control polynucleotide that contains some of the same sequences as the intended target, but is distinguishable from the target by a difference in size or by the presence or absence of a unique sequence such as a restriction site. Homologous controls contain exogenous nucleic acid fragments, i.e., they are not naturally present in a sample, and they are constructed so that they can be amplified with the same primers used to amplify the target. In this approach a synthetic standard is designed to have only slight variations in sequence but readily distinguishable from a target sequence. The sample to be assayed and the synthetic standard are amplified in the same reaction vessel and any variable that may affect amplification should affect both the target and the control equally.

Generally, in the above methods there is a competition between amplification of the control and the target if present, such as competing for binding to primers and for the other reagents such as nucleoside triphosphates and polymerase. The competition results usually because of the availability of only a limited amount of the polymerase. As a result the presence of a high concentration of one of these species can block amplification of the other and thus potentially interfere with detection of either the control or the target. Thus, for example, in order to achieve co-amplification of two DNA species of similar size in PCR, it is usually necessary to begin the amplification with nearly equal concentrations of the two DNA target sequences.

2. Description of the Related Art

U.S. Pat. No. 5,219,727 (Wang, et al.) discusses a method for determining the amount of a target nucleic acid segment in a sample by polymerase chain reaction. The method involves the simultaneous amplification of the target nucleic acid segment and an internal standard nucleic acid segment. The amount of amplified DNA from each segment is determined and compared to standard curves to determine the amount of the target nucleic acid segment present in the sample prior to amplification. The method has particular applicability for determining the quantity of a specific mRNA species in a biological sample. This development is also discussed by Wang, et al., in *Proc. Nat. Acad. Sci. USA* (1989) 86:9717–9721.

Quantitative PCR methods are disclosed by Eeles, et al., in "Polymerase Chain Reaction (PCR): The Technique and Its Applications" (1993) Chapter 6, pages 55–61, R.G. Landes Company.

The elimination of false negatives in nucleic acid amplification is discussed in European Patent Application No. WO 94/04706 (Kievits, et al.). Prior to amplification an internal control is added to the sample. The control has a nucleic acid distinguishable from the analyte nucleic acid that can be amplified with the same amplification reagents as the analyte nucleic acid, preferably a nucleic acid sequence corresponding to the analyte nucleic acid that has been mutated to discriminate it from the analyte nucleic acid.

Celi, et al., describe a rapid and versatile method to synthesize internal standards for competitive PCR in *Nucleic Acids Research* (1993) 21(4):1047.

Gilliland, et al., discuss the analysis of cytokine mRNA and DNA: detection and quantitation by competitive polymerase chain reaction in *Proc. Natl. Acad. Sci. USA* (1990) 87:2725–2729.

PCR mimics:competitive DNA fragments for use as internal standards in quantitative PCR are disclosed by Siebert, et al., in *Biotechniques* (1993) 14(2):244–249.

Piatak, et al., describe quantitative competitive polymerase chain reaction for accurate quantitation of HIV DNA and RNA species in *Biotechnicues* (1993) 14(1):70–80.

Quantitative PCR and RT-PCR in virology is disclosed by Clementi, et al., in *PCR methods and Applications* (1993) 2:191–196.

Competitive polymerase chain reaction using an internal standard: application to the quantitation of viral DNA is discussed by Telenti, et al., *Journal of Virological Methods* (1992) 39:259–268.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science*, 230: 1350–1354. Primer-directed enzymatic amplification of DNA with a thermostable DNA polymerase is described by Saiki, et al., *Science* (1988) 239:487.

U.S. patent applications Ser. Nos. 07/299,282 filed Jan. 19, 1989, now U.S. Pat. No. 5,508,178, describe nucleic acid amplification using a single polynucleotide primer (ASPP). U.S. patent application Ser. No. 07/555,968 filed Jul. 19, 1990, now U.S. Pat. No. 5,439,998 (Aug. 8, 1990), describes a method for producing a molecule containing an intramolecular base-pair structure. A method for introducing defined sequences at the 3'-end of a polynucleotide is described in U.S. patent application Ser. No. 08/140,369, filed Oct. 20, 1993. The disclosures of these five applications are incorporated herein by reference including the references listed in the sections entitled "Description of the Related Art."

Amplification of nucleic acid sequences using oligonucleotides of random sequence as primers is described in U.S. Pat. No. 5,043,272. A single stranded self-hybridizing nucleic acid probe capable of repeatedly hybridizing to itself or other nucleic acids to form an amplified entity is described in U.S. patent application Ser. No. 07/888,058, filed Jul. 22, 1986.

SUMMARY OF THE INVENTION

One embodiment of the present invention relates to a method for forming multiple copies of a target sequence of a target polynucleotide. The method comprises the step of forming extension products of an oligonucleotide primer at least along the target sequence or along an extended polynucleotide primer. The extension products are copies of the target sequence. The improvement of the present invention comprises forming the extension products in the presence of a control oligonucleotide and a control polynucleotide that has a sequence that is hybridizable with the control oligonucleotide. In accordance with the present invention the control oligonucleotide, when bound to the control polynucleotide, reduces the ability of a primer to chain extend along the control polynucleotide. The control oligonucleotide is substantially unable to chain extend along the control polynucleotide. Optionally, the control oligonucleotide is part of the control polynucleotide.

Another aspect of the present invention relates to an improvement in a method for amplifying a target sequence of a target polynucleotide. The method comprises combining a sample suspected of containing the target polynucleotide with reagents for amplifying the target sequence if present and subjecting the combination to conditions wherein the target sequence if present is amplified. The present improvement comprises including in the combination a control oligonucleotide and a control polynucleotide that has a sequence that is hybridizable with the control oligonucleotide. When the control oligonucleotide is bound to the control polynucleotide the ability of a primer to chain extend along the control polynucleotide is reduced. The control oligonucleotide is substantially unable to chain extend along the control polynucleotide. Optionally, the control oligonucleotide is part of the control polynucleotide.

Another embodiment of the present invention is an improvement in a method for forming multiple copies of a target sequence of a single stranded target polynucleotide ("target sequence"). In the method a first oligonucleotide primer ("first primer") is hybridized to the 3'-end of the target sequence. The first primer is extended along at least the target sequence and is capable of hybridizing to, and being extended along, (1) the extended first primer or (2) an extended second oligonucleotide primer ("second primer"). The extended second primer results from the extension of a second primer capable of hybridizing to and extending along a polynucleotide that is complementary (complementary polynucleotide) to the target sequence. The extended first primer is dissociated from the target sequence. The first or the second primer is hybridized to the 3-end of the extended first primer. The first or said second primer is extended along the extended first primer. The extended first primer or the extended second primer is dissociated from the extended first primer. The first primer is hybridized to the 3'-end of the extended first or second primer. The latter three steps are then repeated. The present improvement comprises including, in the same reaction mixture subjected to the above steps, a control oligonucleotide and a control polynucleotide that has a sequence that is hybridizable with the control oligonucleotide. The control oligonucleotide, when bound to the control polynucleotide, reduces the ability of a primer to chain extend along the control polynucleotide. The control oligonucleotide is substantially unable to chain extend along the control polynucleotide. As above, the control oligonucleotide is optionally part of the control polynucleotide.

Another embodiment of the present invention is directed to a method for forming multiple copies of at least one double stranded polynucleotide ("polynucleotide"), where the polynucleotide comprises a single stranded target polynucleotide sequence ("target sequence") and its complementary sequence. The method has a positive internal control. In the method a sample suspected of containing one or more of the double stranded polynucleotides is treated with oligonucleotide primers capable of hybridizing to a portion of each target sequence and its complementary sequence suspected of being present in the sample under conditions for hybridizing the primers to, and extending the primers along, the target sequence and the complementary sequences. The primers are selected such that the extension product formed from one primer, when it is dissociated from its complement, can serve as a template for the formation of the extension product of another primer. Also included in the above are a control oligonucleotide and a control polynucleotide that is amplifiable by at least one of the same primers as the target sequence and has a sequence that is hybridizable with the control oligonucleotide. When the control oligonucleotide is bound to the control polynucleotide, the ability of a primer to chain extend along the control polynucleotide is reduced. The control oligonucleotide is substantially unable to chain extend along the control polynucleotide. Optionally, the control oligonucleotide is part of the control polynucleotide. The conditions allow for the control oligonucleotide to reversibly hybridize to the control polynucleotide. The primer and oligonucleotide primer extension products are dissociated from their templates, if the sequence or sequences are present, to produce single stranded molecules, which are treated with the primer and oligonucleotide primers above under conditions such that a primer extension product is formed using the single strands produced as templates, resulting in amplification of the target sequences and complementary sequences if present. The conditions allow for the extension of the primer along the control polynucleotide.

Another embodiment of the present invention is a method of producing multiple copies of a target sequence of a target polynucleotide. A combination is provided comprising (1) a single stranded polynucleotide having a sequence that is hydridizable with the target sequence and that is flanked at each end by at least partially complementary first and second flanking sequences, (2) an oligonucleotide primer at least a 10-base portion of which at its 3'-end is hybridizable to that member of the first and second flanking sequences that is at the 3'-end of the single stranded polynucleotide, (3) nucleoside triphosphates, (4) a nucleotide polymerase, (5) a control oligonucleotide and (6) a control polynucleotide that is amplifiable by the same primer as the target sequence and has a sequence that is hybridizable with the control oligonucleotide wherein the control oligonucleotide when bound to the control polynucleotide reduces the ability of a primer to chain extend along the control polynucleotide, and wherein the control oligonucleotide is substantially unable to chain extend along the control polynucleotide, and wherein the control oligonucleotide is optionally part of the control polynucleotide. The combination is incubated under conditions for either wholly or partially sequentially or concomitantly (1) dissociating the single stranded polynucleotide from any complementary sequences, (2) hybridizing the polynucleotide primer with the flanking sequence at the 3'-end of the single stranded polynucleotide and with the control polynucleotide and hybridizing the control oligonucleotide to the control polynucleotide, (3) extending the polynucleotide primer along the single stranded polynucleotide to provide a first extended oligonucleotide primer and extending the oligonucleotide primer along the control polynucleotide up to the control oligonucleotide to provide an extended control primer, (4) dissociating the first extended primer and the single stranded polynucleotide and dissociating the control polynucleotide and the control oligonucleotide and the control extended primer, (5) hybridizing the first extended oligonucleotide primer with the oligonucleotide primer and hybridizing the oligonucleotide primer and the control oligonucleotide with the control polynucleotide, (6) extending the oligonucleotide primer along the first extended oligonucleotide primer to provide a second extended oligonucleotide primer and extending the oligonucleotide primer along the control polynucleotide to provide a control extended primer, (7) dissociating the second extended oligonucleotide primer from the first extended oligonucleotide primer and the control oligonucleotide and the control extended primer and the control polynucleotide, and (8) repeating steps (5)–(7) above.

Another embodiment of the present invention is a method for detecting a polynucleotide analyte ("target sequence"). In the method a first oligonucleotide primer ("first primer") is hybridized to the 3'-end of the target sequence and extended along at least the target sequence. The first primer is capable of hybridizing to, and being extended along, (1) extended first primer or (2) an extended second oligonucleotide primer ("second primer") wherein the extended second primer results from the extension of a second primer capable of hybridizing to, and extending along, a polynucleotide that is complementary (complementary polynucleotide) to the target sequence. Extended first primer is dissociated from the target sequence and first or said second primer is hybridized to the 3'-end of extended first primer. First or second primer is extended along extended first primer, and extended first primer or extended second primer is dissociated from extended first primer. First primer is hybridized to the 3'-end of extended first or second primer and the latter three steps are repeated. The above steps are conducted in the presence of a control oligonucleotide and a control polynucleotide that has a sequence that is hybridizable with the control oligonucleotide. The control oligonucleotide when bound to the control polynucleotide reduces the ability of a primer to chain extend along the control polynucleotide and the control oligonucleotide is optionally part of the control polynucleotide. Extended first and/or second primer is detected and the presence thereof indicates the presence of the polynucleotide analyte.

Another embodiment of the present invention relates to an improvement in a method for forming multiple copies of a target sequence of a target polynucleotide. The method comprises the step of forming extension products of a oligonucleotide primer along the target sequence or along an extended oligonucleotide primer. The extension products are copies of the target sequence. The improvement comprises including in the combination a control oligonucleotide and a control polynucleotide that has a sequence that is hybridizable with the control oligonucleotide. When the control oligonucleotide is bound to the control polynucleotide, the ability of a primer to chain extend along the control polynucleotide is reduced. The control oligonucleotide is optionally part of the control polynucleotide.

Another embodiment of the present invention is a kit comprising in packaged combination (a) a control oligonucleotide that is part of a control polynucleotide, which also comprises a sequence that is hybridizable with the control oligonucleotide, wherein the control oligonucleotide is substantially non-chain extendable along the control polynucleotide, (b) a oligonucleotide primer, (c) nucleoside triphosphates, and a nucleotide polymerase.

BRIEF DESCRIPTION OF THE DRAWINGS

FIGS. 1–5 are schematic diagrams depicting alternate embodiments in accordance with the present invention.

DESCRIPTION OF THE SPECIFIC EMBODIMENTS

In its broadest aspect the present invention relates to a method for forming multiple copies of a target sequence of a target polynucleotide. The method comprises the step of forming extension products of a oligonucleotide primer at least along the target sequence or along an extended oligonucleotide primer. The extension products are copies or complements of the target sequence. The improvement of the present invention comprises forming the extension products in the presence of a control oligonucleotide and a control polynucleotide that has a sequence that is hybridizable with the control oligonucleotide. In accordance with the present invention the control oligonucleotide, when bound to the control polynucleotide, reduces the ability of a primer to chain extend along the control polynucleotide. The control oligonucleotide is substantially unable to chain extend along the control polynucleotide. Optionally, the control oligonucleotide is part of the control polynucleotide.

The present method improves the performance of both homologous and heterologous controls by reducing the ability of the control to compete with target amplification. The concept employs a control polynucleotide together with a control oligonucleotide that can bind to the control polynucleotide and, when bound, reduces the efficiency of chain extension of a primer along the control polynucleotide. Preferably, the control polynucleotide is homologous and is amplified by the same primer that is used in an amplification utilizing such a primer. Amplification of the control polynucleotide confirms both the presence and function of the primer and the polymerase used in the primer extension amplification. By controlling the length and base composition of the control oligonucleotide, one can adjust the extent of its binding to the control polynucleotide and thus modulate the efficiency of control amplification. In this way amplification of the control is reduced sufficiently to prevent it from competing with amplification of the target polynucleotide but not reduced to a level that it becomes undetectable.

Before proceeding further with a description of the specific embodiments of the present invention, a number of terms will be defined.

Polynucleotide analyte—a compound or composition to be measured that is a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analytes include nucleic acids, and fragments thereof, from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

| Microorganisms of interest include: | |
|---|---|
| Corynebacteria | |
| *Corynebacterium diphtheria* | |
| Pneumococci | |
| *Diplococcus pneumoniae* | |
| Streptococci | |
| *Streptococcus pyrogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The colliform |
| *Klebsiella pneumoniae* | bacteria |
| *Salmonella typhosa* | |
| *Salmonella choleraesuis* | The Salmonellae |

TABLE I-continued

Microorganisms of interest include:

Salmonella typhimurium
Shigella dysenteria
Shigella schmitzii
Shigella arabinotarda
    The Shigellae
Shigella flexneri
Shigella boydii
Shigella sonnei
Other enteric bacilli
Proteus vulgaris
Proteus mirabilis    Proteus species
Proteus morgani
Pseudomonas aeruginosa
Alcaligenes faecalis
Vibrio cholerae
Hemophilus-Bordetella group    Rhizopus oryzae
Hemophilus influenza, H. ducryi    Rhizopus arrhizua Phycomycetes
Hemophilus hemophilus    Rhizopus nigricans
Hemophilus aegypticus    Sporotrichum schenkii
Hemophilus parainfluenza    Flonsecaea pedrosoi
Bordetella pertussis    Fonsecacea compact
Pasteurellae    Fonsecacea dermatidis
Pasteurella pestis    Cladosporium carrionii
Pasteurella tulareusis    Phialophora verrucosa
Brucellae    Aspergillus nidulans
Brucella melitensis    Madurella mycetomi
Brucella abortus    Madurella grisea
Brucella suis    Allescheria boydii
Aerobic Spore-forming Bacilli    Phialophora jeanselmei
Bacillus anthracis    Microsporum gypseum
Bacillus subtilis    Trichophyton mentagrophytes
Bacillus megaterium    Keratinomyces ajelloi
Bacillus cereus    Microsporum canis
Anaerobic Spore-forming Bacilli    Trichophyton rubrum
Clostridium botulinum    Microsporum adouini
Clostridium tetani    Viruses
Clostridium perfringens    Adenoviruses
Clostridium novyi    Herpes Viruses
Clostridium septicum    Herpes simplex
Clostridium histolyticum    Varicella (Chicken pox)
Clostridium tertium    Herpes Zoster (Shingles)
Clostridium bifermentans    Virus B
Clostridium sporogenes    Cytomegalovirus
Mycobacteria    Pox Viruses
Mycobacterium tuberculosis    Variola (smallpox)
hominis
Mycobacterium bovis    Vaccinia
Mycobacterium avium    Poxvirus bovis
Mycobacterium leprae    Paravaccinia
Mycobacterium paratuberculosis    Molluscum contagiosum
Actinomycetes (fungus - like bacteria)    Picornaviruses
Actinomyces Isaeli    Poliovirus
Actinomyces bovis    Coxsackievirus
Actinomyces naeslundii    Echoviruses
Nocardia asteroides    Rhinoviruses
Nocardia brasiliensis    Myxoviruses
The Spirochetes    Influenza (A, B, and C)
Treponema pallidum    Spirillum minus    Parainfluenza (1-4)
Treponema pertenue    Streptobacillus    Mumps Virus
    monoiliformis    Newcastle Disease Virus
Treponema carateum    Measles Virus
Borrelia recurrentis    Rinderpest Virus
Leptospira icterohemorrhagiae    Canine Distemper Virus
Leptospira canicola    Respiratory Syncytial Virus
Trypanasomes    Rubella Virus
Mycoplasmas    Arboviruses
Mycoplasma pneumoniae
Other pathogens    Eastern Equine Eucephalitis Virus
Listeria monocytogenes    Western Equine Eucephalitis Virus
Erysipelothrix rhusiopathiae    Sindbis Virus
Streptobacillus moniliformis    Chikugunya Virus
Donvania granulomatis    Semliki Forest Virus
Bartonella bacilliformis    Mayora Virus
Rickettsiae (bacteria-like    St. Louis Encephalitis Virus
parasites)
Rickettsia prowazekii    California Encephalitis Virus
Rickettsia mooseri    Colorado Tick Fever Virus

TABLE I-continued

Microorganisms of interest include:

| | |
|---|---|
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis nonA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |
| *Aspergillus fumigatus* | |
| *Mucor corymbifer* (*Absidia corymbifera*) | |

Also included are genes, such as hemoglobin gene for sickle-cell anemia, cystic fibrosis gene, oncogenes, cDNA, and the like.

The polynucleotide analyte, where appropriate, may be cleaved to obtain a fragment that contains a target polynucleotide sequence, for example, by shearing or by treatment with a restriction endonuclease or other site specific chemical cleavage method.

For purposes of this invention, the polynucleotide analyte, or a cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90°–100° C. for a period of about 1 to 10 minutes to produce denatured material.

Amplification of nucleic acids or polynucleotides—any method that results in the formation of one or more copies of a nucleic acid or polynucleotide molecule (exponential amplification) or in the formation of one or more copies of the complement of a nucleic acid or polynucleotide molecule (linear amplification).

Exponential amplification of nucleic acids or polynucleotides—any method that results in the formation of one or more copies of a nucleic acid or polynucleotide molecule present in a medium. One such method for the enzymatic amplification of specific double stranded sequences of DNA is known as the polymerase chain reaction (PCR), as described above. This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification is mentioned above and involves amplification of a single stranded polynucleotide using a single oligonucleotide primer. The single stranded polynucleotide that is to be amplified contains two non-contiguous sequences that are complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving a nucleic acid amplification is the nucleic acid sequence based amplification (NASBA). This method is a promoter-directed, enzymatic process that induces in vitro continuous, homogeneous and isothermal amplification of specific nucleic acid.

Another method for amplifying a specific group of nucleic acids is the Q-beta-replicase method, which relies on the ability of Q-beta-replicase to amplify its RNA substrate exponentially.

Linear amplification of nucleic acids or polynucleotides—any method that results in the formation of one or more copies of the complement of one strand of a nucleic acid or polynucleotide molecule, usually a nucleic acid or polynucleotide analyte, present in a medium. Thus, one difference between linear amplification and exponential amplification is that the latter produces copies of both strands of a nucleic acid whereas the former produces the complementary strand of a polynucleotide. In linear amplification the number of complements formed increases as a linear function of time as opposed to exponential amplification where the number of copies is an exponential function of time.

Target sequence of a target polynucleotide—a sequence of nucleotides to be identified, usually existing within a portion (target polynucleotide) or all of a polynucleotide analyte, the identity of which is known to an extent sufficient to allow preparation of various primers and other molecules necessary for conducting an amplification of the target sequence contained within the target polynucleotide. In general, in primer extension amplification primers hybridize to, and are extended along (chain extended), at least the target sequence within the target polynucleotide and, thus, the target sequence acts as a template. The extended primers are chain "extension products." The target sequence usually lies between two defined sequences but need not. In general, the primers and other probe polynucleotides hybridize with the defined sequences or with at least a portion of such target polynucleotide, usually at least a ten nucleotide segment at the 3'-end thereof and preferably at least 15, frequently 20 to 50 nucleotide segment thereof. The target sequence usually contains from about 30 to 5,000 or more nucleotides, preferably 50 to 1,000 nucleotides. The target polynucleotide is generally a fraction of a larger molecule or it may be substantially the entire molecule (polynucleotide analyte). The minimum number of nucleotides in the target polynucleotide sequence is selected to assure that the presence of target polynucleotide in a sample is a specific indicator of the presence of polynucleotide analyte in a sample. Very roughly, the sequence length is usually greater than about 1.6 log L nucleotides where L is the number of base pairs in the genome of the biologic source of the sample. The maximum number of nucleotides in the target polynucleotide is normally governed by the length of the polynucleotide analyte and its tendency to be broken by shearing, or other processes during isolation and any procedures required to prepare the sample for assay and the efficiency of detection and/or amplification of the sequence.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, preferably, 6 to 50 nucleotides, more preferably, 10 to 30 nucleotides in length.

Control polynucleotide—a polynucleotide having a sequence that is hybridizable with a control oligonucleotide. Such a sequence can lie at any place within the amplifiable portion of the control polynucleotide. Accordingly, it may lie in the region involved in initiation of chain extension, i.e., the priming site, or it may lie within the sequence that serves as a template for extending the primer along the control polynucleotide. Preferably, the control polynucleotide is homologous. Preferably, the control polynucleotide has a sequence that is hybridizable with a primer used for amplification of a target polynucleotide. In some instances the control polynucleotide contains the control oligonucleotide as an integral part thereof. The control polynucleotide is usually comprised of a sequence of at least 30 nucleotides, preferably, 100 to 4000 nucleotides, more preferably, 200 to 2000 nucleotides in length. When binding occurs within a control polynucleotide priming site, the effect of binding is to interfere with binding of the primer and thus to reduce the efficiency of amplification of the control polynucleotide. When binding occurs at a position that serves as a template for primer extension, the extension rate will be lower and the efficiency of amplification of the control polynucleotide will again be reduced.

Control oligonucleotide—an oligonucleotide that may be a separate molecule or an integral part of a control polynucleotide. The control oligonucleotide is shorter than the control polynucleotide and is usually comprised of a sequence of at least 5 nucleotides, preferably, 5 to 50 nucleotides, more preferably, 5 to 30 nucleotides in length.

The control oligonucleotide can be a priming site for the amplification of the control polynucleotide, in which case it, of course, is part of the control polynucleotide. When the control oligonucleotide is an integral part of the control polynucleotide, it may be part of the template sequence between the two priming sites of the control polynucleotide in which case it is able to bind internally to a complementary region within the template sequence. Alternatively, the control oligonucleotide is one of the priming sites of the control polynucleotide in which case the two priming sites are complementary to each other. Amplification of this type of control polynucleotide requires only one primer. In either case, when the control oligonucleotide is an integral part of the control polynucleotide, there are two sequences within the control polynucleotide that can bind to each other to form a stem-loop structure. The existence of such a structure diminishes the efficiency of the amplification. If the control oligonucleotide sequence is located too far away from its complementary binding site, its ability to interfere with amplification is reduced. Therefore, when the control oligonucleotide is an integral part of the control polynucleotide, it is located preferably at a distance of from 5 to 300 nucleotides, more preferably, 25 to 200 nucleotides, from the sequence with which it can hybridize. The particular distance is selected to provide the desired degree of amplification of the control polynucleotide. When the control oligonucleotide is an integral part of the control polynucleotide adjusting the relative position of the control oligonucleotide and its complement has the same effect as adjusting the concentration of the control oligonucleotide when it is present as a separate molecule.

The control oligonucleotide and the control polynucleotide are substantially incapable of extending along each other. This is achieved in a number of ways. For example, the control oligonucleotide and the control polynucleotide can hybridize to each other at sites other than the 3'-ends of each strand. Alternatively, the 3'-end of one strand can be blocked by a group that cannot undergo chain extension, such as, for example, a 3'-phosphate, a 3'-terminal dideoxy, an abasic ribophosphate, a polymer or surface, or other means for inhibiting chain extension and that strand is designed to bind to the other strand at other than its 3'-end. In another approach the 3'-end of the control oligonucleotide binds to the 5'-end of the control polynucleotide. Accordingly, extension of the 3'-end of the control oligonucleotide does not occur because the non-hybridized portion of the control oligonucleotide has no template on which to extend and the 3'-end of the control polynucleotide does not extend because it is not hybridized to a complementary sequence. All of the above procedures for such modification are well known in the art. Furthermore, other procedures for such modifications will be suggested to those skilled in the art.

The design and preparation of the control oligonucleotide is important in performing the methods of this invention. One consideration is that the control oligonucleotide hybridize to the control polynucleotide and reduce the ability of a primer to chain extend along the control polynucleotide. Accordingly, the control oligonucleotide should be partially bound to the control polynucleotide at the temperature of chain extension in the amplification reaction so as to cause a reduced efficiency of amplification of the control polynucleotide relative to the efficiency in the absence of the control oligonucleotide. The degree of reduction in efficiency is selected empirically so that sufficient amplified control polynucleotide is formed to permit it to be detected without substantially interfering with the amplification of the target polynucleotide. The efficiency can be controlled in a number of ways. For example, the control oligonucleotide can be rich in guanine (G) and cytidine (C). Series of G's and C's relatively uninterrupted by A's and T's are particularly useful in reducing amplification efficiency because their tight binding inhibits dissociation during primer extension. Accordingly, the control oligonucleotide may be adjusted with the above in mind. Other techniques to inhibit dissociation can be used such as increasing the length of the control oligonucleotide or attaching the control oligonucleotide to the control polynucleotide and limiting the distance between the control oligonucleotide and the site to which it binds on the control polynucleotide. Alternatively, the control oligonucleotide can be provided with one or more covalently attached small molecules that can intercalate into or otherwise bind the double strand. A large variety of small molecule binders are available such as ethidium, acridinium, and phenazinium ions, psoralin, daunomycin, mitomycin and the like. In each of these preparations the small molecule may be attached to any convenient atom of a base, e.g., the 8 position of G or A or the 4-amino group of C or the 5-methyl group of T, or the group may be attached to a ribose carbon or to a phosphate, for example, by alkylation of a phosphorothioate. Alternatively, the control oligonucleotide may be synthesized with alternative atoms in place of the phosphate linkages. In particular, uncharged linkers can provide tighter binding to a complementary strand. Uncharged linkers that can be used are phosphonates, phosphites, amides, methylene dioxy groups and the like. The synthesis of these types of oligonucleotide analogs are known in the art.

Oligonucleotide primer(s)—an oligonucleotide that is usually employed in a chain extension on a polynucleotide template such as in, for example, an amplification of a nucleic acid. The oligonucleotide primer is usually a synthetic nucleotide that is single stranded, containing a sequence at its 3'-end that is capable of hybridizing with a defined sequence of the target polynucleotide. Normally, an oligonucleotide primer has at least 80%, preferably 70%, more preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the oligonucleotide primer will be at least as great as the defined sequence of the target polynucleotide, namely, at least ten nucleotides, preferably at least 15 nucleotides and generally from about 10 to 200, preferably 20 to 50, nucleotides.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine (G), inosine, and derivatives and analogs thereof. The pyrimidine bases include cytosine (C), thymine (T), uracil (U), and derivatives and analogs thereof. Nucleoside triphosphates include deoxyribonucleoside triphosphates such as dATP, dCTP, dGTP and dTTP and ribonucleoside triphosphates such as rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like. Nucleotide—a base-sugar-phosphate combination that is the monomeric unit of nucleic acid polymers, i.e., DNA and RNA.

Modified nucleotide—is the unit in a nucleic acid polymer that results from the incorporation of a modified nucleoside triphosphate during an amplification reaction and therefore becoming part of the nucleic acid polymer.

Nucleoside—is a base-sugar combination or a nucleotide lacking a phosphate moiety.

Nucleotide polymerase—a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the single stranded portion of the polynucleotide template. Usually, the catalysts are enzymes, such as DNA polymerases, for example, prokaryotic DNA polymerase (I, II, or III), T4 DNA polymerase, T7 DNA polymerase, Klenow fragment, reverse transcriptase, Vent DNA polymerase, Pfu DNA polymerase, Taq DNA polymerase, and the like, derived from any source such as cells, bacteria, such as *E. coli*, plants, animals, virus, thermophilic bacteria, and so forth.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Homologous or substantially identical polynucleotides—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Non-contiguous—two sequences are non-contiguous, there being at least one, usually at least 10 nucleotides, lying between two segments of a polynucleotide sequence to which the two sequences are hybridized.

Contiguous—sequences are contiguous when there are no nucleotides between two segments of a polynucleotide sequence to which the two sequences are hybridized.

Copy—means a sequence that is a direct identical copy of a single stranded polynucleotide sequence as differentiated from a sequence that is complementary to the sequence of such single stranded polynucleotide.

Means for extending a primer—a nucleotide polymerase or a single stranded template polynucleotide having a sequence other than at its 3'-end that can hybridize to at least the 3'-end of the primer or both. Means for extending a primer also includes nucleoside triphosphates or analogs thereof capable of acting as substrates for the enzyme and other materials and conditions required for enzyme activity such as a divalent metal ion (usually magnesium), pH, ionic strength, organic solvent (such as formamide), and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA—DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label or reporter group or reporter molecule—a member of the signal producing system. Usually the label or reporter group or molecule is conjugated to or becomes bound to a polynucleotide probe or a oligonucleotide primer and is capable of being detected directly or, through a specific binding reaction, and can produce a detectible signal. Labels include a oligonucleotide primer or specific polynucleotide sequence that can provide a template for amplification or ligation or act as a ligand such as for a repressor protein. Preferably, the oligonucleotide primer will have, or be capable of having, a label. In general, any label that is detectable can be used. The label can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—the signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. The signal-producing system is described more fully in U.S. patent application Ser. No. 07/555,968, filed Jul. 19, 1990 now U.S. Pat. No. 5,439,998 (Aug. 8, 1990), the relevant disclosure of which is incorporated herein by reference.

Ancillary Materials—Various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above the present invention provides an improvement in nucleic acid amplification reactions by providing for a positive control. Accordingly, the present invention avoids false negatives in such amplification reactions.

One embodiment of the present invention is depicted in FIG. 1. In this embodiment an amplification by PCR is chosen by way of example and not limitation. The sample suspected of containing the nucleic acid or target polynucleotide (TPN) having a target sequence (TPNS) to be amplified by PCR is combined with two different oligonucleotide primers (PP1 and PP2), a nucleotide polymerase, nucleoside triphosphates and a control polynucleotide (CPN). CPN has at its 5' end a sequence (CON) that serves as a control oligonucleotide in this particular embodiment. CPN also has at its 3'-end a sequence CPNS that can hybridize with CON and with PP1. Conditions are chosen to achieve thermal cycling of the reaction mixture. Under such conditions PP1 hybridizes with CPNS of CPN and with primer binding site PBS1 of TPN if the latter is present. Extension of PP1 along CPN and TPN, respectively, yields extended PP1 that is the complement of CPN (CCPN) for the control and the complement of TPN (EPP1) for the amplification of target. During the reaction PP2 hybridizes at PBS2 with, and is extended along, the complementary strand of TPN to form extended PP2 (EPP2). Molecules EPP1 and EPP2 serve as templates for primers PP2 and PP1, respectively. In addition, both CPN and CCPN serve as templates for primer PP1. CPN functions as a control polynucleotide as follows. When TPN is present in the sample, PP1 hybridizes with both TPN and CPN. However, the extension of PP1 along CPN is less efficient than its extension along TPN because of the binding of the control oligonucleotide (CON) to CPNS, which in this particular embodiment results from the internal hybridization in CPN (CON with CPNS) that can compete with the hybridization of PP1 with CPNS. The extension of PP1 along TPN is more efficient. The number of copies and complements of CPN resulting from the hybridization of PP1 with and extension along CPN to give extension products that are copies of and complements of CPN is diminished when TPN is present in the sample. When TPN is not present in the sample, the extension of PP1 proceeds along CPN and many more copies and complements of CPN are formed because there is no competing reaction involving the extension of PP1 that is more efficient. By selecting the number of nucleotides between CON and CPNS, the efficiency of the amplification of CPN can be controlled. Generally, the number of nucleotides between CON and CPNS in this embodiment is about 50 to 300, preferably, 100 to 200. Another way in which the efficiency of the extension of PP1 along CPN can be controlled is by adjusting the concentration of CPN. The concentration of CPN is dependent on other factors such as the concentration of other reagents, the temperature of the reaction, and the like and generally is about 0.1 femtomolar to 0.1 nanomolar.

Another embodiment of the present invention is depicted in FIG. 2. In this embodiment an amplification by PCR is again chosen by way of example and not limitation. The sample suspected of containing the nucleic acid or target polynucleotide (TPN) having a target sequence (TPNS) to be amplified by PCR is combined with two different oligonucleotide primers (PP1 and PP2), a nucleotide polymerase, nucleoside triphosphates and two different control polynucleotides (CPN1 and CPN2). CPN1 has at its 5'-end a sequence (CON1) that serves as a control oligonucleotide with respect to the amplification of that strand of TPN to which PP1 hybridizes. CPN1 also has at its 3'-end a sequence CPNS1 that can hybridize with CON1. CPN2 has at its 5' end a sequence (CON2) that serves as a control oligonucleotide. CPN2 also has at its 3'-end a sequence CPNS2 that can hybridize with CON2. Conditions are chosen to achieve thermal cycling of the reaction mixture. Under the conditions chosen PP1 hybridizes with CPN1 and with TPN if the latter is present. Extension of PP1 along CPN1 and TPN, respectively, yields extended PP1 that is the complement of CPN1 (CCPN1) for the control and the complement of TPN (EPP1) for the amplification of target. During the reaction PP2 hybridizes with, and is extended along, the complementary strand of TPN to form extended PP2 (EPP2) and CPN2 to form extended CPN2 (CCPN2). Molecules EPP1 and EPP2 serve as templates for primers PP2 and PP1, respectively. In addition, CPN1, CPN2, CCPN1 and CCPN2 serve as templates for primer PP1. CPN1 and CPN2 function as controls as follows. When TPN is present in the sample, PP1 hybridizes with both TPN and CPN1. However, the extension of PP1 along CPN1 is less efficient than its extension along TPN because of the binding of the control oligonucleotide (CON1) to CPNS1, which in this particular embodiment results from the internal hybridization in CPN1 (CON1 with CPNS1) that can compete with the hybridization of PP1 with CPNS1. The extension of PP1 along TPN is more efficient. Likewise, when TPN is present in the sample, PP2 hybridizes with both the other strand of TPN and CPN2. However, the extension of PP2 along CPN2 is less efficient than its extension along TPN because of the binding of the control oligonucleotide (CON2) to CPNS2, which in this particular embodiment results from the internal hybridization in CPN2 (CON2 with CPNS2) that can compete with the hybridization of PP2 with CPNS2. The extension of PP2 along TPN is more efficient. The number of copies and complements of CPN1 and CPN2 resulting from the hybridization of PP1 and PP2 with and extension along CPN1 and CPN2, respectively, to give extension products that are copies of and complements of CPN1 and CPN2, respectively, is diminished when TPN is present in the sample. When TPN is not present in the sample, the extension of PP1 proceeds along CPN1 and the extension of PP2 proceeds along CPN2 and many more copies and complements of CPN1 and CPN2 are formed because there are no competing reactions involving the extension of PP1 and PP2, respectively, that are more efficient. By selecting the number of nucleotides between CON1 and CPNS1 and between CON2 and CPNS2, the efficiency of the amplification of CPN1 and CPN2 can be controlled. Generally, the number of nucleotides between CON1 and CPNS1 and CON2 and CPNS2, respectively, in this embodiment is as set forth above for the embodiment in FIG. 1.

Another embodiment of the present invention is depicted in FIG. 3. In this embodiment an amplification by a single oligonucleotide primer (ASPP) is chosen by way of example and not limitation. The sample suspected of containing the nucleic acid or target polynucleotide (TPN) having a target sequence (TPNS) to be amplified is combined with an oligonucleotide primer PP1, a strand-switch blocker SSB (as described in U.S. patent application Ser. No. 08/140,369 filed Oct. 20, 1993, the relevant disclosure of which is incorporated herein by reference), a nucleotide polymerase, nucleoside triphosphates and a control polynucleotide (CPN). CPN has at its 5'-end a sequence (CON) that serves as a control oligonucleotide. CPN also has at its 3'-end a sequence CPNS that can hybridize with CON. Conditions are chosen to achieve thermal cycling of the reaction mixture. Under such conditions PP1 hybridizes with CPN and with TPN if the latter is present. Extension of PP1 along CPN yields extended PP1 that is the complement of CPN (CCPN) for the control. Extension of PP1 along TPN proceeds until PP1 encounters SSB, at which point PP1 extends along that portion of SSB that is not hybridized to TPN yielding extended PP1 (EPP1) that has two sequences that hybridize to one another and that flank a sequence CTPNS, which is the complement of TPNS. EPP1 is then amplified during the thermal cycling by the single primer PP1. Molecules EPP1 serve as templates for primer PP1. In addition, both CPN and CCPN serve as templates for primer PP1. CPN functions as a control as follows. When TPN is present in the sample, PP1 hybridizes with both TPN and CPN. However, the extension of PP1 along CPN is less efficient than its extension along TPN because of the binding of the control oligonucleotide (CON) to CPNS, which in this particular embodiment results from the internal hybridization in CPN (CON with CPNS) that can compete with the hybridization of PP1 with CPNS. The extension of PP1 along TPN is more efficient. The number of copies and complements of CPN resulting from the hybridization of PP1 with and extension along CPN to give extension products that are copies of and complements of CPN is diminished when TPN is present in the sample. When TPN is not present in the sample, the extension of PP1 proceeds along CPN and many more copies and complements of CPN are formed because there is no competing reaction involving the extension of PP1 that is more efficient. By selecting the number of nucleotides between CON and CPNS, the efficiency of the amplification of CPN can be controlled. Generally, the number of nucleotides between CON and CPNS in this embodiment is determined as described above. As mentioned above, the efficiency of the extension of PP1 along CPN also can be controlled by adjusting the concentration of CPN.

Another embodiment of the present invention is depicted in FIG. 4. In this embodiment an amplification by PCR is chosen by way of example and not limitation. The sample suspected of containing the nucleic acid or target polynucleotide (TPN) having a target sequence (TPNS) to be amplified by PCR is combined with two different oligonucleotide primers (PP1 and PP2), a nucleotide polymerase, nucleoside triphosphates and a control polynucleotide (CPN). CPN has at its 5' end a sequence (S1) that hybridizes with a sequence (CPNS) at its 3'-end that can hybridize with PP1. A control oligonucleotide (CON), as a molecule separate from CPN, is utilized in this particular embodiment. CPN has a sequence (S2) to which CON hybridizes. Conditions are chosen to achieve thermal cycling of the reaction mixture. Under such conditions PP1 hybridizes with CPNS of CPN and with primer binding site PBS1 of TPN if the latter is present. Extension of PP1 along CPN and TPN, respectively, yields extended PP1 that is the complement of CPN (CCPN) for the control and the complement of TPN (EPP1) for the amplification of target. During the reaction PP2 hybridizes at PBS2 with, and is extended along, the complementary strand of TPN to form extended PP2 (EPP2). Molecules EPP1 and EPP2 serve as templates for primers PP2 and PP1, respectively. In addition, both CPN and CCPN serve as templates for primer PP1. CPN functions as a control polynucleotide as follows. When TPN is present in the sample, PP1 hybridizes with both TPN and CPN. However, the extension of PP1 along CPN is less efficient than its extension along TPN because of the binding of the control oligonucleotide (CON) to S2 of CPN that can compete with the hybridization of PP1 with CPNS. The extension of PP1 along TPN is more efficient. The number of copies and complements of CPN resulting from the hybridization of PP1 with and extension along CPN to give extension products that are copies of and complements of CPN is diminished when TPN is present in the sample. When TPN is not present in the sample, the extension of PP1 proceeds along CPN and many more copies and complements of CPN are formed because there is no competing reaction involving extension of PP1 that is more efficient. By selecting the number of nucleotides between CON and S2, the efficiency of the amplification of CPN can be controlled. Generally, the number of nucleotides between CON and S2 in this embodiment is determined as described above. Another way in which the efficiency of the extension of PP1 along CPN can be controlled is by adjusting the concentration of CPN as discussed above.

Another embodiment of the present invention is depicted in FIG. 5. In this embodiment an amplification by PCR is chosen by way of example and not limitation. The sample suspected of containing the nucleic acid or target polynucleotide (TPN) having a target sequence (TPNS) to be amplified by PCR is combined with two different oligonucleotide primers (PP1 and PP2), a nucleotide polymerase, nucleoside triphosphates and a control polynucleotide (CPN). CPN has at its 5' end a sequence (S1) that hybridizes with a sequence (CPNS) at its 3'-end that can hybridize with PP1. A control oligonucleotide (CON) is utilized in this particular embodiment and is part of CPN, which also has a sequence (S2) to which CON hybridizes. Conditions are chosen to achieve thermal cycling of the reaction mixture. Under such conditions PP1 hybridizes with CPNS of CPN and with primer binding site PBS1 of TPN if the latter is present. Extension of PP1 along CPN and TPN, respectively, yields extended PP1 that is the complement of CPN (CCPN) for the control and the complement of TPN (EPP1) for the amplification of target. During the reaction PP2 hybridizes at PBS2 with, and is extended along, the complementary strand of TPN to form extended PP2 (EPP2). Molecules EPP1 and EPP2 serve as templates for primers PP2 and PP1, respectively. In addition, both CPN and CCPN serve as templates for primer PP1. CPN functions as a control polynucleotide as follows. When TPN is present in the sample, PP1 hybridizes with both TPN and CPN. However, the extension of PP1 along CPN is less efficient than its extension along TPN because of the internal binding of the control oligonucleotide (CON) to S2 of CPN that can compete with the hybridization of PP1 with CPNS. For the molecules of CPN that are internally hybridized, PP1 is extended only to the point of the hybridized CON and S2. The extension of PP1 along TPN is more efficient. The number of copies and complements of CPN resulting from the hybridization of PP1 with and extension along CPN to give extension products that are copies of and complements of CPN is diminished when TPN is present in the sample. When TPN is not present in the sample, the extension of PP1 proceeds along CPN and many more copies and complements of CPN are formed because there is no competing reaction involving extension of PP1 that is more efficient. By selecting the number of nucleotides between CON and S2, the efficiency of the amplification of CPN can be controlled. Generally, the number of nucleotides between CON and S2 in this embodiment is determined as described above. Another way in which the efficiency of the extension of PP1 along CPN can be controlled is by adjusting the concentration of CPN as discussed above. It is noteworthy in the above embodiment that internal hybridization can also occur in CPN by virtue of the binding of CPNS and S1. However, in this embodiment the number of nucleotides (indicated by the squiggly lines in FIG. 5) between S1 and CPNS is great enough to substantially reduce the internal hybridization of these sequences in CPN. Accordingly, the internal hybridization that occurs primarily results from the binding of CON and S2. Furthermore, the latter binding can be enhanced as described above. The present method has application where the target polynucleotide sequence is DNA or RNA.

Another embodiment of the invention concerns a method for detecting the presence of a polynucleotide analyte in a sample suspected of containing the polynucleotide analyte. A medium containing the sample is treated as described above to yield a target polynucleotide from the polynucleotide analyte, if present, or the polynucleotide analyte itself is the target polynucleotide. The medium is then combined with reagents for conducting an amplification. The particular reagents depend on the particular amplification protocol chosen. The target polynucleotide is then subjected to the above method in accordance with the present invention to generate multiple copies of the target polynucleotide sequence, which are then detected. Then, an examination is conducted for the presence of extended primer, the presence thereof indicating the presence of the polynucleotide analyte. Generally, the amplification is conducted for a sufficient number of cycles to provide an accurate detection of the polynucleotide analyte. Conditions such as pH, temperature, times, and so forth, chosen for conducting the present method are dependent on the particular method of amplification selected. The conditions set out below apply primarily to exponential amplification by one or two primers by extension of those primers. The following description sets forth such appropriate conditions, which are subject to modification by those skilled in the art depending on the specific reagents and other molecules chosen for any particular application.

Where the polynucleotide analyte is RNA, it can first be converted to DNA by means of a primer and reverse transcriptase, or, as mentioned above, the nucleotide polymerase used can be reverse transcriptase.

In carrying out the methods in accordance with the present invention including amplification, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and preferably in the range of about 6–8. The pH and temperature are chosen and varied, as the case may be, so as to cause, either simultaneously or sequentially, dissociation of any internally hybridized sequences, hybridization of the primers and any other probes with the target polynucleotide sequence, hybridization of the oligonucleotide primer with target polynucleotide sequences, hybridization of the control oligonucleotide with the control polynucleotide, extension of the primer(s), and dissociation of the extended primer(s). In some instances, a compromise is made in optimizing the speed, efficiency, and specificity of these steps depending on whether it is desired to perform the above steps sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the methods. Normally, in conducting the methods the medium is cycled between two or three temperatures. The temperatures for the methods generally range from about 10° to 105° C., more usually from about 40° to 99° C., preferably 50° to 98° C. The exact temperatures can be varied depending on the salt concentration, pH, solvents used, length of and composition of the target polynucleotide sequence and the primer. Relatively low temperatures of from about 30° to 65° C. can be employed for the extension steps, while denaturation and hybridization can be carried out at a temperature of from about 50° to 105° C.

In some situations it is desirable to cause hybridization and extension to occur only after denaturation of the template polynucleotide is complete. This has the advantage of increasing the fidelity of replication and can be achieved by preheating the template to at least 80° C., preferably 90°–100° C., prior to combining it with the polymerase and/or nucleoside triphosphates that will usually also be preheated.

Where the present method is utilized in single primer amplification or in PCR, the method is conducted for a time sufficient to achieve a desired number of copies of the extended primer or a sequence complementary thereto. This, in turn, depends on the purpose for which the amplification is conducted, such as, for example, an assay for a polynucleotide analyte. Generally, the time period for conducting the method will be from about 1 to 10 minutes per cycle and any number of cycles can be used from 1 to as high as 200 or more, usually 5 to 80, frequently 10–60. As a matter of convenience it is usually desirable to minimize the time period and the number of cycles. In general, the time period for a given degree of amplification can be shortened, for example, by selecting concentrations of nucleoside triphosphates sufficient to saturate the nucleotide polymerase and by increasing the concentrations of nucleotide polymerase and oligonucleotide primer. Generally, the time period for conducting the method will be from about 5 to 200 minutes. As a matter of convenience, it will usually be desirable to minimize the time period.

The concentration of the nucleotide polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The amount of the target polynucleotide sequence which is to be copied can be as low as one or two molecules in a sample but generally may vary from about $10^2$ to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M. The amount of the oligonucleotide primer(s) will be at least as great as the number of copies desired and will usually be $10^{-13}$ to $10^{-8}$ moles per sample, where the sample is 1–1,000 $\mu$L. Usually, the primer(s) are present in at least $10^{-9}$M, preferably $10^{-7}$M, and more preferably at least about $10^{-6}$M. Preferably, the concentration of the oligonucleotide primer (s) is substantially in excess over, preferably at least 100 times greater than, more preferably, at least 1000 times greater than, the concentration of the target polynucleotide sequence. Such a relative concentration results in minimizing any potential hybridization between the control oligonucleotide and the target polynucleotide. In addition, however, the concentration of at least one oligonucleotide primer can be used to control the efficiency of the control reaction. In such a circumstance the concentration is about $10^{-10}$ to $10^{-6}$M.

The concentration of the nucleoside triphosphates in the medium can vary widely; preferably, these reagents are present in an excess amount. The nucleoside triphosphates are usually present in $10^{-6}$ to $10^{-2}$M, preferably $10^{-5}$ to $10^{-3}$M.

The order of combining of the various reagents to form the combination may vary. In accordance with the present invention the control reagents are present in the amplification reaction mixture during the amplification reaction. Generally, the target polynucleotide sequence is obtained from a sample containing such sequence or a polynucleotide analyte that has been-treated to obtain such sequence. Generally, the target polynucleotide sequence is combined with a pre-prepared combination of nucleoside triphosphates and nucleotide polymerase. The oligonucleotide primer(s) may be included in the prepared combination or may be added subsequently. Furthermore, the reagents for conducting the control, which include a control polynucleotide and a control oligonucleotide, if the latter is not part of the control polynucleotide, are included in the combination of reagents for conducting an amplification. However, simultaneous addition of all of the above, as well as other step-wise or sequential orders of addition, may be employed.

The concentration and order of addition of reagents and conditions for the method are governed generally by the desire to maximize the number of copies of the extended primer(s) and the rate at which such copies are formed and the fidelity of replication as well as achieving an accurate and reliable control. Generally, it is desirable to increase the number of copies of the extended primer by at least a factor of $10^2$, preferably a factor of $10^4$, more preferably $10^6$ or more. For the control the main concern is that the control reaction provide a reliable indication of the performance of the amplification reagents. As mentioned above, selecting the concentration of the control reagents can control the efficiency of the control reaction in relation to the amplification reaction. The parameters for such concentration of the control reagents are set forth above.

In carrying out the method of the invention as applied to the detection of a polynucleotide analyte, the considerations as to media, pH, temperature, and times can be as described above.

While the concentrations of the various reagents are generally determined by the concentration range of interest of the polynucleotide analyte, the final concentration of each of the reagents is normally determined empirically to optimize the sensitivity of the assay over the range of interest and provide for reliable control. The concentration of the other reagents in an assay generally is determined following the same principles as set forth above for the amplification method. The primary considerations is that a sufficient number of copies of extended primer(s) be produced in relation to the polynucleotide analyte sequence so that such copies can be readily detected and provide an accurate determination of the polynucleotide analyte and that the control reaction provide a reliable indication of the performance of the amplification reagents.

The copies of extended primer(s) can be detected in numerous ways. For example, in the present method, molecules of the oligonucleotide primer can be labeled with a reporter molecule such as a ligand, a small organic molecule, a polynucleotide sequence, a protein, support, a member of an operator-repressor pair, intercalation dye and the like. Extended primer(s) can be detected by means of a reporter molecule covalently bonded to a probe. The probe has a nucleotide sequence that is homologous or complementary to a portion of the target nucleotide sequence other than those sequences to which the primers bind. Any standard method for specifically detecting nucleic acid sequences can be used.

It should be noted that both the amplified target and the amplified control must be detected. In one approach separate probes are employed, each separate probe bearing a label different from the other. In this way the different products in the amplification reaction are differentiated. In another approach the amplified products are differentiated on the basis of different physical properties associated with different lengths. In many circumstances gel or capillary electrophoresis is employed for differentiating among the products with respect to length. The above are provided by ay of example and not limitation. Any method that can differentiate among the amplified products may be used.

One method for detecting nucleic acids is to employ nucleic acid probes. One method utilizing probes is described in U.S. patent application Ser. No. 773,386, filed Sep. 6, 1985, now U.S. Pat. No. 4,868,104 (Sep. 19, 1989) the disclosure of which is incorporated herein by reference.

Other assay formats and detection formats are disclosed in U.S. patent applications Ser. No. 07/229,282 filed Jan. 19, 1989, now U.S. Pat. No. 5,508,178 U.S. patent application Ser. No. 07/555,323, 07/555,968, filed Jul. 19, 1990, now U.S. Pat, No. 5,439,998 (Aug. 8, 1990), and U.S. patent application Ser. No. 08/140,369, filed Oct. 20, 1993, which have been incorporated herein by reference.

Examples of particular labels or reporter molecules and their detection can be found in U.S. patent application Ser. No. 07/555,968 filed Jul. 19, 1990, now U.S. Pat. No. 5,439,998 (Aug. 8, 1990) the relevant disclosure of which is incorporated herein by reference.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Various techniques can be employed for preparing a control oligonucleotide, a control polynucleotide, an oligonucleotide primer, or other polynucleotides, utilized in the present invention. They can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide primer and other polynucleotides can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol*, 101, 20–78.

Other methods of oligonucleotide synthesis include phosphotriester and phosphodiester methods (Narang, et al. (1979) *Meth. Enzymol* 68: 90) and synthesis on a support (Beaucage, et al. (1981) *Tetrahedron Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Oligonucleotides containing at least one monophosphate having a 3' terminus comprised of a nucleotide monophosphate in which at least one phosphate oxygen is replaced by sulfur can be prepared according to known techniques. Oligonucleotide synthesis can be carried out as described above up to the point where introduction of the phosphorussulfur bond is desired. The phosphorus-sulfur bond can be introduced in a number of ways such as, for example, oxidations utilizing a thiolating reagent such as a diacyldisulfide or tetraethyl thiuram disulfide, which are commercially available. The remaining nucleotides are then introduced. Other methods of preparing phosphorothioate containing polynucleotides are described in WO9008838, WO8911486, U.S. Pat. No. 4,910,300, EP318245, the relevant disclosures of which are incorporated herein by reference. Other methods of preparing a phosphorothioate containing polynucleotide are described by (a) Yau, et al., *Tetrahedron Lett*. (1990)31(14): 1953–1956; (b) Brill, et al., *ibid*. (1989) 30(48):6621–6624; (c) Caruthers, et al., *Nucleic Acids Symp. Ser*. (1989)21: 119–120; (d) Caruthers, et al., *Nucleosides Nucleotides* (1988)8(5–6): 1011–1014; (e) Brill, et al., *J. Am. Chem. Soc*. (1989)111(6): 2321–2322.

As mentioned above, in some instances the 3'-end of a polynucleotide is modified to prevent reaction with template dependent DNA polymerase or to append a binding sequence. Usually, an unannealed or unhybridized DNA tail on the 3' end is all that is necessary. However, the 3'-end can be modified, for example, by introducing an abasic ribophosphate or other unnatural group at the 3' end during solid phase synthesis or introduction of a dideoxynucleotide or a ribonucleotide followed by oxidation of the ribose with periodate followed by reductive amination of the resulting dialdehyde with borohydride and a bulky amine such as aminodextran. The details for carrying out the above modifications are well-known in the art and will not be repeated here.

As a matter of convenience, predetermined amounts of reagents employed in the present invention can be provided in a kit in packaged combination. A kit can comprise in packaged combination (a) a control polynucleotide comprising a control oligonucleotide and a sequence that is hybridizable with the control oligonucleotide, (b) an oligonucleotide primer that hybridizes to the control polynucleotide, (c) nucleoside triphosphates, and (d) a nucleotide polymerase. The kit can also include a second oligonucleotide primer where the primers are related in that a product of the extension of one along a target sequence serves as a template for the extension of the other.

In assaying for a polynucleotide analyte in a sample, a kit useful in the present method can comprise, in packaged combination with other reagents mentioned above, reagents for forming a target polynucleotide sequence from a polynucleotide analyte. Furthermore, the oligonucleotide primer can be labeled or can be provided with groups to render the sequence labeled or bound to a support. The kit can further include a labeled polynucleotide probe capable of binding to an amplified target polynucleotide sequence. The kits above can further include in the packaged combination nucleoside triphosphates such as nucleoside triphosphates, e.g., deoxyadenosine triphosphate (dATP), deoxyguanosine triphosphate (dGTP), deoxycytidine triphosphate (dCTP) and deoxythymidine triphosphate (dTTP). The kit can further include members of a signal producing system and also various buffered media, some of which may contain one or more of the above reagents.

The relative amounts of the various reagents in the kits can be varied widely to provide for concentrations of the reagents which substantially optimize the reactions that need to occur during the present method and to further substantially optimize the sensitivity of the assay and the reliability of the control. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

In accordance with an embodiment of FIG. 1 a double stranded target DNA is derived from M. tuberculosis BCG (from Dr. Chris Green, Stanford Research International, Menlo Park, Calif.) containing 650 base pairs ("Current Protocols in Molecular Biology," Vol. 1: pp 2.4.1–2.4.2, editor Frederick Ausubel, et al., John Wiley & Sons) by a process of standard bacterial genomic DNA isolation (the "target DNA"). The control polynucleotide is a double stranded DNA fragment of 126 base pairs derived from plasmid M13mp19 by PCR, i.e., Polymerase Chain Reaction, using 5' tailed primers to incorporate the 25-base pair sequences described below. The 5'-terminus of the single strands of the control polynucleotide contains a 25-base pair sequence, namely, 5'ACT-GGT-AGA-GGC-GGC-GAT-GGT-TGA-A3' (SEQ ID NO: 1) synthesized on a Pharmacia Gene Assembler (Pharmacia Biotech, Piscataway, N.J.), which serves as a control polynucleotide, and the 3'-terminus of the single strands of the control polynucleotide contains a 25-base pair sequence that is the full complement of the above 25-base pair sequence at the 5'-terminus, namely, 5' T-TCA-ACC-ATC-GCC-GCC-TCT-ACC-AGT 3' (SEQ ID NO:2) synthesized on a Pharmacia Gene Assembler (Pharmacia Biotech, Piscataway, N.J.), which serves as a control polynucleotide sequence.

Amplifications are conducted by polymerase chain reaction in accordance with the disclosure of U.S. Pat. Nos. 4,683,195, 4,683,202, 4,800,159, 4,965,188 and 5,008,182, which disclose the polymerase chain reaction, the relevant disclosures of which are incorporated herein by reference. The amplifications are carried out using $10^4$, $10^3$, $10^2$, 10 and 0 target DNA molecules, respectively. A 100 microliter assay mixture is prepared having 1 micromolar concentration each of first and second primers (see (a) Sjobring, et al., *Journal of Infectious Diseases*, (1992) 166: 177–180), (b) Eisenach, et al., *Journal of Infectious Diseases*, (1992) 161:977–981, and (c) Bocart,et al., *Am Rev Respir Dis*, (1992) 145:1142–1148), 250 micromolar deoxynucleoside triphosphates (dATP, dCTP, dGTP and dTTP) (from Pharmacia Biotech, Piscataway, N.J.), 2.5 units of AmpliTaq DNA polymerase (from Perkin Elmer-Roche Molecular Systems, Branchburg, N.J.) in a 1× buffer containing 10 mM Tris (pH 8.3), 50 mM KCl, 2.5 mM MgCl2, supplied as a 10× stock from the vendor. The assay mixture is subjected to the following temperature cycles: 1 minute at 94° C., 1 minute at 66° C. and 1 minute at 72° C. repeated 45 times. Then, a 10% aliquot of the reaction mixture is subjected to electrophoreses on 1.5% agarose gels and is stained with ethidium bromide. Amplified fragments were detected by examination under UV light. Amplification of control polynucleotide is achieved along with amplification of the target DNA molecule in accordance with the present invention.

In another embodiment in accordance with FIG. 4, the above protocol is followed with the following changes. The control polynucleotide is a molecule containing 126-base pairs. The 5'-terminus of the single strands of the control polynucleotide contains to a 25-base pair sequence, namely, 5'ACT-GGT-AGA-GGC-GGC-GAT-GGT-TGA-A3' (SEQ ID NO:1) synthesized on a Pharmacia Gene Assembler (Pharmacia Biotech, Piscataway, N.J.), and the 3'-terminus of the single strands of the control polynucleotide contains a 25-base pair sequence that is the full complement of the above 25-base pair sequence attached to the 5'-terminus, namely, 5' T-TCA-ACC-ATC-GCC-GCCTCT-ACC-AGT 3'(SEQ ID NO:2) synthesized on a Pharmacia Gene Assembler (Pharmacia Biotech, Piscataway, N.J.), and a portion of the sequence lying between the above sequences is an intermediate sequence, namely, 5' CAC-TTT-GCG-GGC-ACC-GTA-AAC-ACC-GTA-GTT 3' (SEQ ID NO:3) that is fully complementary to a control oligonucleotide, namely, 5' AAC-TAC-GGT-GTT-TAC-GGT-GCC-CGC-AAA-GTG 3' (SEQ ID NO:4). The above control oligonucleotide is synthesized on a Pharmacia Gene Assembler (Pharmacia Biotech, Piscataway, N.J.). Primers employed are as described above for the embodiment of FIG. 1. The control oligonucleotide is present in the assay mixture at a concentration equimolar to the primer. In this embodiment the first primer binds to the control polynucleotide at the control polynucleotide sequence but the extension of the primer along the control polynucleotide is impeded by the binding of the control oligonucleotide to the intermediate sequence. The first primer also binds to the 3'-end of one of the strands of the target DNA and is extended along such strand. The second primer binds to and is extended along the other of the strands of the target DNA. Amplification of control polynucleotide is achieved along with amplification of the target DNA molecule in accordance with the present invention.

EXAMPLES

The invention is demonstrated further by the following illustrative examples. Temperatures are in degrees centigrade (°C.) and parts and percentages are by weight, unless otherwise indicated.

Tris—Tris(hydroxymethyl)aminomethane-HCl (a 10× solution) from BioWhittaker, Walkersville, Md.

DTT—dithiothreitol from Sigma Chemical Company, St. Louis, Mo.

Single stranded target DNA was derived from M. tuberculosis BCG (from Dr. Chris Green from Stanford Research International, Menlo Park, Calif.) containing 650 base pairs ("Current Protocols in Molecular Biology", (1994) Vol.1: pp 2.4.1–2.4.2, editor Frederick Ausubel, et al., John Wiley & Sons) by a process of standard bacterial genomic DNA isolation (the "target DNA"). The control polynucleotide was a double stranded DNA fragment of 126 base pairs derived from plasmid M13mp19 by PCR using 5' tailed primers to incorporate the 25-base pair sequences described below. The 5'-terminus of the single strands of the control polynucleotide contains a 25-base pair sequence, namely, 5'ACT-GGT-AGA-GGC-GGC-GAT-GGT-TGA-A3' (SEQ ID NO:1) synthesized on a Pharmacia Gene Assembler (Pharmacia Biotech, Piscataway, N.J.), which served as a control polynucleotide, and the 3'-terminus of the single strands of the control polynucleotide contains a 25-base pair sequence that is the full complement of the above 25-base pair sequence at the 5'-terminus, namely, 5' T-TCA-ACC-ATC-GCC-GCC-TCT-ACC-AGT 3'(SEQ ID NO:2) synthesized on a Pharmacia Gene Assembler (Pharmacia Biotech, Piscataway, N.J.), which served as a control polynucleotide sequence. The primer was a 25-base pair molecule having the sequence 5'ACT-GGT-AGA-GGC-GGC-GAT-GGT-TGA-A3'(SEQ ID NO:1) synthesized on a Pharmacia Gene Assembler (Pharmacia Biotech, Piscataway, N.J.). The strand switch blocker was a 70-base pair molecule having the sequence 5'ACT-GGT-AGA-GGC-GGC-GAT-GGT-TGA-ATA-ACC-CTG-AAT-TCA-GGG-TTA-GCC-ACA-CTT-TGC-GGG-CAC-CGT-AAA-C3' (SEQ ID NO:5) synthesized on a Pharmacia Gene Assembler (Pharmacia Biotech, Piscataway, N.J.).

The amplification was conducted in accordance with the disclosure of U.S. patent application Ser. No. 08/140,369 filed Oct. 20, 1993, the relevant disclosure of which is incorporated herein by reference. The amplifications were carried out using $10^4$, $10^3$, $10^2$, 10 and 0 target DNA molecules, respectively. A 100 microliter assay mixture was prepared having 1 micromolar primer, 50 nanomolar strand switch blocker, 250 micromolar deoxynucleoside triphosphates (dATP, dCTP, dGTP and dTTP) (from Pharmacia Biotech, Piscataway, N.J.), 5 units of Pfu DNA polymerase (from Stratagene, San Diego, Calif.) in a 1× buffer containing 10 mM Tris (pH 8.8), 50 mM KCl, 1.5 mM MgCl2, 7.5 mM DTT and 0.1% Triton X-100. The assay mixture was subjected to the following temperatures: an initial denaturation for 4 minutes at 95° C. followed temperature cycle of 1 minute at 94° C., 1 minute at 66° C. and 1 minute at 72° C. repeated 45 times. Then, a 10% aliquot of the reaction mixture was subjected to electrophoreses on 1.5% agarose gels and stained with ethidium bromide. Amplified fragments were detected by examination under UV light.

The above protocol was repeated at various concentrations and sizes of control polynucleotide. The results are summarized in the following Table 1.

TABLE 1

| Length of control polynucleotide (bases) | Control molecules per tube | Target molecules/tube* | | | | |
|---|---|---|---|---|---|---|
| | | 0 | 10 | $10^2$ | $10^3$ | $10^4$ |
| 126 | $10^4$ | +/– | +/+ | +/+ | +/+ | |
| | $10^5$ | +/– | +/– | +/+ | +/+ | |
| | $10^6$ | +/– | +/– | +/– | +/+ | |
| | $10^7$ | +/– | +/– | +/– | +/– | |
| | $10^8$ | +/– | +/– | +/– | +/– | |
| 142 | $10^2$ | +/– | –/+ | –/+ | –/+ | –/+ |
| | $10^3$ | +/– | +/– | +/+ | +/+ | +/+ |
| | $10^4$ | +/– | +/– | +/+ | +/+ | +/+ |
| | $10^5$ | +/– | +/– | +/+ | +/+ | +/+ |
| | $10^6$ | +/– | +/– | +/– | +/– | +/+ |
| | $10^7$ | +/– | +/– | +/– | +/– | +/– |
| | $10^8$ | +/– | +/– | +/– | +/– | +/– |

*The numerator shows the occurrence (+) or absence (–) of amplification of the control polynucleotide. The denominator shows the occurrence (+) or absence (–) of amplification of target DNA.

The above results indicate that a control polynucleotide was found to be amplified along with amplification of the target DNA. The above examples demonstrate that a control oligonucleotide and a control polynucleotide in accordance with the present invention can be utilized effectively in amplification of nucleic acids. Accordingly, the present invention provides for a reliable control reaction to determine whether amplification reagents and conditions, and other amplification related items such as instrumentation, are functioning properly and whether the lack of detection of a polynucleotide analyte is a true indication of the absence of the polynucleotide analyte.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

What is claimed is:

1. In a method for forming multiple copies of a target sequence of a target polynucleotide, said method comprising the step of forming extension products of a first oligonucleotide primer capable of specifically hybridizing to, and being extended at least along, said target sequence or along an extended first oligonucleotide primer, said extension products being copies of said target sequence, the improvement which comprises forming said extension products in the presence of a control oligonucleotide and a control polynucleotide wherein said control polynucleotide has a subsequence that is specifically hybridizable with said control oligonucleotide and wherein said control oligonucleotide when bound to said control polynucleotide reduces the ability of a second oligonucleotide primer, which may be the same as or different from said first oligonucleotide primer and which specifically hybridizes to said control polynucleotide, to chain extend along said control polynucleotide and wherein said control oligonucleotide is optionally part of said control polynucleotide.

2. The method of claim 1 wherein said subsequence lies outside a second sequence of said control polynucleotide wherein said second sequence is hybridizable with said second oligonucleotide primer.

3. The method of claim 1 wherein said subsequence lies within a second sequence of said control polynucleotide wherein said second sequence is hybridizable with said second oligonucleotide primer.

4. The method of claim 3 wherein said subsequence lies at the 5'-end of said second sequence.

5. The method of claim 1 wherein said first oligonucleotide primer and said second oligonucleotide primer are the same.

6. The method of claim 1 wherein the presence of amplified target sequence is detected, the presence of said amplified target sequence being an indication of the presence of said target polynucleotide.

7. A method for forming multiple copies of a target sequence of a single stranded target polynucleotide in a reaction mixture, said method comprising:

(a) hybridizing to a 3'-end of said target sequence a first oligonucleotide primer wherein said target sequence comprises a subsequence that has the same sequence as the sequence of the first oligonucleotide primer or comprises a subsequence that has the same sequence as that of a second oligonucleotide primer, (b) extending said first oligonucleotide primer along at least said target sequence to form an extended first oligonucleotide primer sequence, (c) dissociating said extended first oligonucleotide primer sequence from said target sequence, (d) hybridizing, to a 3'-end of said extended first oligonucleotide primer sequence, said first or said second oligonucleotide primer wherein said first or said second oligonucleotide primer is capable of hybridizing to, and extending along, said extended first oligonucleotide primer sequence, (e) extending said first or said second oligonucleotide primer along said extended first oligonucleotide primer sequence to form a sequence complementary to said extended first oligonucleotide primer sequence, (f) dissociating said complementary sequence from said extended first oligonucleotide primer sequence, (g) hybridizing, to a 3'-end of said complementary sequence, said first oligonucleotide primer, and (h) repeating steps (e)–(g), the improvement comprising including, in said reaction mixture subjected to steps (a)–(g) above, a control oligonucleotide and a control polynucleotide that includes a subsequence that is specifically hybridizable with said control oligonucleotide and a subsequence that is specifically hybridizable with said first oligonucleotide primer or said second oligonucleotide primer, wherein said control oligonucleotide when hybridized to said control polynucleotide reduces the ability of said first oligonucleotide primer or said second oligonucleotide primer to chain extend along said control polynucleotide and wherein said control oligonucleotide is optionally part of said control polynucleotide.

8. The method of claim 7 wherein the subsequence of the control polynucleotide to which the control oligonucleotide hybridizes lies outside the subsequence to which said first oligonucleotide primer or said second oligonucleotide primer hybridizes.

9. The method of claim 7 wherein, the subsequence of the control polynucleotide to which the control oligonucleotide hybridizes lies within the subsequence to which said first oligonucleotide primer or said second oligonucleotide primer hybridizes.

10. The method of claim 9 wherein the subsequence of the control polynucleotide to which the control oligonucleotide hybridizes lies at the 5'-end of the subsequence to which said first oligonucleotide primer or said second oligonucleotide primer hybridizes.

11. The method of claim 7 wherein the presence of said copies of said target sequence are detected, the presence thereof being an indication of the presence of said target polynucleotide.

12. The method of claim 7 wherein said control oligo nucleotide is 5 to 30 nucleotides in length.

13. The method of claim 7 wherein said control oligonucleotide is present in the reaction mixture at a concentration of from about 1 nM to 100 uM.

14. The method of claim 7 wherein said control oligonucleotide is part of said control polynucleotide and is located within 5 to 300 nucleotides of said subsequence.

15. The method of claim 7 wherein the repeating of steps (e)–(g) is achieved by repeated temperature cycling.

16. The method of claim 15 wherein temperature cycling is repeated at least 3 times.

17. The method of claim 7 wherein said target polynucleotide is DNA.

18. The method of claim 7 wherein said extending is carried out in the presence of nucleoside triphosphates and nucleotide polymerase.

19. The method of claim 7 wherein only said first primer is used and said target sequence contains at its 5' end at least a 10 base sequence hybridizable with a sequence at the 3' end of said target sequence to which said first primer hybridizes.

20. The method of claim 7 wherein said first and second primers are different and extended first primer is a template for said second primer and said extended second primer is a template for said first primer.

21. A method for forming multiple copies of at least one double stranded polynucleotide, said polynucleotide comprising a single stranded target polynucleotide sequence and its complementary sequence, said method having a positive internal control, said method comprising:

(a) treating a sample suspected of containing one or more of said double stranded polynucleotides with (i) oligonucleotide primers capable of specifically hybridizing to a portion of each target polynucleotide sequence and its complementary sequence suspected of being present in said sample under conditions for hybridizing said oligonucleotide primers to and extending said oligonucleotide primers along said target polynucleotide sequence and said complementary sequence, wherein said oligonucleotide primers are selected such that the extension product formed from one oligonucleotide primer, when it is dissociated from its complement, can serve as a template for the formation of the extension product of another oligonucleotide primer, (ii) a control oligonucleotide, and (iii) a control polynucleotide that is amplifiable by at least one of the same oligonucleotide primers as said target polynucleotide sequence and has a subsequence that is specifically hybridizable with said control oligonucleotide wherein said control oligonucleotide when bound to said control polynucleotide reduces the ability of said at least one of the same oligonucleotide primers to chain extend along said control polynucleotide and wherein said control oligonucleotide is optionally part of said control polynucleotide, said conditions allowing for said control oligonucleotide to hybridize to said control polynucleotide so as to cause a reduced efficiency of amplification of the control polynucleotide relative to the efficiency of said amplification in the absence of said control oligonucleotide, (b) dissociating oligonucleotide primer extension products from their templates if the target polynucleotide sequence is present to produce single stranded molecules and (c) treating the single stranded molecules produced in step (b) with said oligonucleotide primers of step (a) under conditions such that an oligonucleotide primer extension product is formed using the single strands produced in step (b) as templates, resulting in amplification of the target polynucleotide sequence and complementary sequence if present, said conditions allowing for the extension of said same oligonucleotide primer along said control polynucleotide.

22. The method of claim 21 wherein said subsequence lies outside a second sequence of said control polynucleotide wherein said second sequence is hybridizable with said same oligonucleotide primer.

23. The method of claim 21 wherein said subsequence lies within a second sequence of said control polynucleotide wherein said second sequence is specifically hybridizable with said same oligonucleotide primer.

24. The method of claim 23 wherein said subsequence lies at the 5'-end of said second sequence.

25. The method of claim 21 wherein the presence of said oligonucleotide primer extension products are detected, the presence thereof indicating the presence of said polynucleotide.

26. The method of claim 21 wherein said control oligo nucleotide is 5 to 30 nucleotides in length.

27. The method of claim 21 wherein said control oligonucleotide is present in the reaction mixture at a concentration of from about 1 nM to 100 uM.

28. The method of claim 21 wherein said control oligonucleotide is part of said control polynucleotide and is located within 5 to 300 nucleotides of said subsequence.

29. The method of claim 21 wherein said conditions of step (c) are achieved by repeated temperature cycling.

30. The method of claim 29 wherein temperature cycling is repeated at least 3 times.

31. The method of claim 21 wherein said polynucleotide is DNA.

32. The method of claim 21 wherein said extending is carried out in the presence of nucleoside triphosphates and nucleotide polymerase.

33. The method of claim 21 comprising adding to the product of step (c) a labeled oligonucleotide probe for each target polynucleotide sequence and complementary sequence being amplified wherein said probe is capable of specifically hybridizing to said target polynucleotide sequence or said complementary sequence or a mutation thereof and determining whether hybridization has occurred.

34. A method of producing multiple copies of a target sequence of a target polynucleotide, which comprises:

(a) providing in combination (I) a single stranded polynucleotide having a sequence that is specifically hybridizable with said target sequence and that is flanked at each end by first and second flanking sequences that are specifically hybridizable to one another, (II) an oligonucleotide primer at least a 10 base portion of which at its 3'-end is hybridizable to whichever of said first and second flanking sequences is at the 3'-end of said single stranded polynucleotide, (III) nucleoside triphosphates, (IV) nucleotide polymerase, (V) a control oligonucleotide and (VI) a control polynucleotide that is amplifiable by the same primer as in (II) and has a subsequence that is hybridizable with said control oligonucleotide wherein said control oligonucleotide when bound to said control polynucleotide reduces the ability of a primer to chain extend along said control polynucleotide and wherein said control oligonucleotide is optionally part of said control polynucleotide and (b) incubating said combination under conditions for either wholly sequentially or partially sequentially or concomitantly (I) dissociating said single stranded polynucleotide from any complementary sequences, (II) hybridizing said oligonucleotide primer with the flanking sequence at the 3'-end of said single stranded polynucleotide and with said control polynucleotide and hybridizing said control oligonucleotide to said control polynucleotide, (III) extending said oligonucleotide primer along said single stranded polynucleotide to provide a first extended oligonucleotide primer and extending said oligonucleotide primer along said control polynucleotide up to the point of hybridization of said control oligonucleotide to said control polynucleotide to provide an extended control primer, (IV) dissociating said first extended primer and said single stranded polynucleotide and dissociating said control polynucleotide and said control oligonucleotide and said control extended primer, (V) hybridizing said first extended oligonucleotide primer with said oligonucleotide primer and hybridizing said oligonucleotide primer and said control oligonucleotide with said control polynucleotide, (VI) extending said oligonucleotide primer along said first extended oligonucleotide primer to provide a second extended oligonucleotide primer and extending said oligonucleotide primer along said control polynucleotide to provide a control extended oligonucleotide primer, (VII) dissociating said second extended oligonucleotide primer from said first extended oligonucleotide primer and said control oligonucleotide and said control extended primer and said control polynucleotide, and (VII) repeating steps (V)–(VII) above.

35. The method of claim 34 wherein said subsequence lies outside a second sequence of said control polynucleotide wherein said second sequence is hybridizable with said oligonucleotide primer.

36. The method of claim 34 wherein said subsequence lies within a second sequence of said control polynucleotide wherein said second sequence is hybridizable with a said oligonucleotide primer.

37. The method of claim 36 wherein said subsequence lies at the 5'-end of said second sequence.

38. The method of claim 34 wherein the presence of extended oligonucleotide primers are detected, the presence thereof indicating the presence or amount of said target polynucleotide.

39. The method of claim 38 wherein said oligonucleotide primer is labeled with a reporter group.

40. The method of claim 34 wherein said control oligonucleotide is 5 to 30 nucleotides in length.

41. The method of claim 34 wherein said control oligonucleotide is present in the reaction mixture at a concentration of from about 1 nM to 100 uM.

42. The method of claim 34 wherein said control oligonucleotide is part of said control polynucleotide and is located within 5 to 300 nucleotides of said sequence.

43. The method of claim 34 wherein the repeating of steps (e)–(g) is achieved by repeated temperature cycling.

44. The method of claim 43 wherein temperature cycling is repeated at least 3 times.

45. The method of claim 34 wherein said target polynucleotide is DNA.

46. A method for detecting a polynucleotide analyte, said method comprising:

(a) hybridizing to the 3'-end of said polynucleotide analyte a first oligonucleotide primer, (b) extending said first oligonucleotide primer along at least said polynucleotide analyte, said first oligonucleotide primer being capable of specifically hybridizing to, and being extended along, (I) said extended first oligonucleotide primer wherein said polynucleotide analyte comprises a first sequence that is hybridizable with said first oligonucleotide primer and a second sequence that is hybridizable with said first sequence or (II) an extended second oligonucleotide primer wherein said extended second oligonucleotide primer is produced by the extension of a second oligonucleotide primer capable of specifically hybridizing to and extending along a complementary polynucleotide that is complementary to said polynucleotide analyte, (c) dissociating extended first oligonucleotide primer from said polynucleotide analyte, (d) hybridizing, to the 3'-end of said extended first oligonucleotide primer, said first or said second oligonucleotide primer, (e) extending said first or said second oligonucleotide primer along said extended first oligonucleotide primer, (f) dissociating said extended first oligonucleotide primer or said extended second oligonucleotide primer from said extended first oligonucleotide primer, (g) hybridizing, to the 3'-end of said extended first or second oligonucleotide primer, said first oligonucleotide primer, (h) repeating steps (e)–(g), wherein steps (a)–(g) above are conducted in the presence of a control oligonucleotide and a control polynucleotide wherein said control polynucleotide has a subsequence that is specifically hybridizable with said control oligonucleotide and wherein said control oligonucleotide when bound to said control polynucleotide reduces the ability of said first or second oligonucleotide primer which specifically hybridizes to said control polynucleotide to chain extend along said control polynucleotide and wherein said control oligonucleotide is optionally part of said control polynucleotide, and (i) detecting said extended first and/or second oligonucleotide primer, the presence thereof indicating the presence of said polynucleotide analyte.

47. The method of claim 46 wherein said subsequence lies outside a second sequence of said control polynucleotide wherein said second sequence is hybridizable with said first or said second primer.

48. The method of claim 46 wherein said subsequence lies within a second sequence of said control polynucleotide wherein said second sequence is hybridizable with said first or said second primer.

49. The method of claim 48 wherein said subsequence lies at the 5'-end of said second sequence.

50. The method of claim 46 wherein said control oligonucleotide is 5 to 30 nucleotides in length.

51. The method of claim 46 wherein said control oligonucleotide is present in the reaction mixture at a concentration of from about 1 nM to 100 uM.

52. The method of claim 46 wherein said control oligonucleotide is part of said control polynucleotide and is located within 5 to 300 nucleotides of said sequence.

53. The method of claim 46 wherein the repeating of steps (e)–(g) is achieved by repeated temperature cycling.

54. The method of claim 53 wherein temperature cycling is repeated at least 3 times.

55. The method of claim 46 wherein said polynucleotide analyte is DNA.

56. The method of claim 46 wherein said extending is carried out in the presence of nucleoside triphosphates and nucleotide polymerase.

57. The method of claim 46 wherein only said first primer is used and said polynucleotide analyte contains at its 5' end at least a 10 base sequence hybridizable with a sequence at the 3' end of said polynucleotide analyte to which said first primer hybridizes.

58. The method of claim 46 wherein said first and second primers are different and extended first primer is a template for said second primer and said extended second primer is a template for said first primer.

59. In a method for forming multiple copies of a target sequence of a target polynucleotide, said method comprising the step of forming extension products of an oligonucleotide primer along said target sequence or along an extended oligonucleotide primer, said extension products being copies of said target sequence, the improvement which comprises forming said extension products in the presence of a control oligonucleotide and a control polynucleotide wherein said control polynucleotide has a subsequence that is specifically hybridizable with said control oligonucleotide and said oligonucleotide primer, and wherein said control oligonucleotide when bound to said control polynucleotide reduces the ability of said oligonucleotide primer to chain extend along said control polynucleotide and wherein said control oligonucleotide is optionally part of said control polynucleotide.

60. A kit comprising in packaged combination:

(a) a control oligonucleotide that is part of a control polynucleotide, which also comprises a sequence (hybridizable sequence) that is hybridizable with said control oligonucleotide, said control oligonucleotide being non-chain extendable along said control polynucleotide (b) an oligonucleotide primer that is hybridizable with said hybridizable sequence of said control polynucleotide, (c) nucleoside triphosphates, and (d) a nucleotide polymerase.

61. The kit of claim 60 comprising a second oligonucleotide primer, said oligonucleotide primers being related in that a product of the extension of one of said first or said second oligonucleotide primer along a target sequence serves as a template for the extension of the other of said first or said second oligonucleotide primer.

* * * * *